US012564358B2

(12) United States Patent
Shahandeh et al.

(10) Patent No.: US 12,564,358 B2
(45) Date of Patent: Mar. 3, 2026

(54) SYSTEMS AND METHODS FOR REMOTE PROGRAMMING OF, AND OTHER FOLLOW-UP CAPABILITIES WITH, LEADLESS PACEMAKERS

(71) Applicant: Pacesetter, Inc., Sylmar, CA (US)

(72) Inventors: Reza Shahandeh, Tarzana, CA (US); Gabriel Mouchawar, Valencia, CA (US); Mostafa Sadeghi, Los Angeles, CA (US); Matthew G. Fishler, Scotts Valley, CA (US); Suresh Gurunathan, Palo Alto, CA (US); Benjamin T. Persson, Saratoga, CA (US)

(73) Assignee: Pacesetter, Inc., Sylmar, CA (US)

( * ) Notice: Subject to any disclaimer, the term of this patent is extended or adjusted under 35 U.S.C. 154(b) by 1037 days.

(21) Appl. No.: 17/587,456

(22) Filed: Jan. 28, 2022

(65) Prior Publication Data

US 2022/0313161 A1      Oct. 6, 2022

Related U.S. Application Data

(63) Continuation-in-part of application No. 17/222,242, filed on Apr. 5, 2021, now Pat. No. 11,918,817.

(Continued)

(51) Int. Cl.
*A61B 5/00*          (2006.01)
*A61B 5/283*        (2021.01)
(Continued)

(52) U.S. Cl.
CPC ............ *A61B 5/686* (2013.01); *A61B 5/0006* (2013.01); *A61B 5/0022* (2013.01); *A61B 5/283* (2021.01); *A61B 5/6898* (2013.01)

(58) Field of Classification Search
CPC .. A61N 1/37252; A61N 1/056; A61N 1/3702; A61N 1/3706; A61N 1/37223;
(Continued)

(56) References Cited

U.S. PATENT DOCUMENTS 7,043,305 B2 * 5/2006 KenKnight ............ G16H 20/40
                                                                 607/32
8,942,818 B2   1/2015 Markowitz
(Continued)

OTHER PUBLICATIONS

Restriction Requirement dated Dec. 29, 2022, U.S. Appl. No. 17/222,279, filed Apr. 5, 2021.
(Continued)

*Primary Examiner* — Brian T Gedeon
(74) *Attorney, Agent, or Firm* — Pearl Cohen Zedek Latzer Baratz LLP

(57)          ABSTRACT

Described herein are methods, devices, and systems that enable a remote non-implantable device (RNID) to send commands to a leadless pacemaker (LP) implanted within a patient. The RNID provide commands to a local non-implantable device (LNID) over one or more communication networks, and the LNID sends the commands to a second implantable device (SID) by transmitting radio frequency (RF) communication signals, which include the commands, using an antenna of the LNID. After receiving the commands from the LNID, by receiving RF communication signals that include the commands using an antenna of the SID, the SID transmits conductive communication signals, which include the commands, using electrodes of the SID. The LP receives the commands from the SID by receiving the conductive communication signals, which include the commands, using electrodes of the LP, and the LP performs command responses based on the commands that originated from the RNID.

9 Claims, 10 Drawing Sheets

Related U.S. Application Data

(60) Provisional application No. 63/243,601, filed on Sep. 13, 2021.

(51) Int. Cl.

| | |
|---|---|
| *A61N 1/362* | (2006.01) |
| *A61N 1/368* | (2006.01) |
| *A61N 1/37* | (2006.01) |
| *A61N 1/372* | (2006.01) |
| *A61N 1/39* | (2006.01) |

(58) Field of Classification Search
CPC ............ A61N 1/37258; A61N 1/37512; A61N 1/3756; A61N 1/3727; A61N 1/37247; A61N 1/37235; H04B 13/005; H04W 76/10

See application file for complete search history.

(56) References Cited

U.S. PATENT DOCUMENTS

| | | | | |
|---|---|---|---|---|
| 9,168,383 | B2 | 10/2015 | Jacobson et al. | |
| 9,592,393 | B2 | 3/2017 | Stahmann et al. | |
| 9,867,990 | B2 | 1/2018 | Cinbis | |
| 10,213,610 | B2 | 2/2019 | Maile et al. | |
| 10,722,720 | B2 | 7/2020 | Stahmann et al. | |
| 10,946,202 | B2 | 3/2021 | Maile et al. | |
| 11,219,771 | B2* | 1/2022 | Swenson | A61B 5/0031 |
| 2011/0301435 | A1 | 12/2011 | Albert et al. | |
| 2014/0221859 | A1 | 8/2014 | Albert | |
| 2015/0174414 | A1 | 6/2015 | Stahmann et al. | |
| 2015/0196769 | A1 | 7/2015 | Stahmann et al. | |
| 2016/0059007 | A1 | 3/2016 | Koop | |
| 2016/0121128 | A1* | 5/2016 | Fishler | H04W 52/04 |
| | | | | 607/32 |
| 2016/0206892 | A1 | 7/2016 | Demmer | |
| 2016/0271406 | A1 | 9/2016 | Maile et al. | |
| 2018/0021583 | A1 | 1/2018 | Ciciarelli et al. | |
| 2018/0035920 | A1 | 2/2018 | Gunderson et al. | |
| 2018/0056075 | A1 | 3/2018 | Hahn et al. | |
| 2018/0078777 | A1 | 3/2018 | Wu et al. | |
| 2018/0140853 | A1 | 5/2018 | Maile et al. | |
| 2018/0178022 | A1 | 6/2018 | Koop et al. | |
| 2018/0200525 | A1 | 7/2018 | Schilling et al. | |
| 2018/0207433 | A1 | 7/2018 | Koop et al. | |
| 2019/0201701 | A1 | 7/2019 | Balczewski et al. | |
| 2020/0086128 | A1* | 3/2020 | Rondoni | G06F 21/606 |
| 2021/0308470 | A1 | 10/2021 | Fishler et al. | |
| 2021/0308471 | A1 | 10/2021 | Fishler et al. | |
| 2022/0212019 | A1 | 7/2022 | Lee et al. | |
| 2024/0165414 | A1 | 5/2024 | Fishler et al. | |

OTHER PUBLICATIONS

Response to Office Action dated Jan. 20, 2023, European Patent Application No. 22155857.0-1126.

Response to Restriction Requirement dated Feb. 10, 2023, U.S. Appl. No. 17/222,279, filed Apr. 5, 2021.

Non-final Office Action dated Jan. 15, 2025, U.S. Appl. No. 17/701,132, filed Mar. 22, 2022.

Extended European Search Report dated Jan. 24, 2025, European Patent Application No. 24212218.2-1122.

U.S. Appl. No. 18/429,714, filed Feb. 1, 2024.

Notice of Allowance dated Oct. 12, 2023, U.S. Appl. No. 17/222,242, filed Apr. 5, 2021.

Non-final Office Action dated Jun. 21, 2023, U.S. Appl. No. 17/222,242, filed Apr. 5, 2021.

Notice of Allowance dated Nov. 8, 2023, U.S. Appl. No. 17/222,279, filed Apr. 5, 2021.

Response to Office Action dated Aug. 7, 2023, U.S. Appl. No. 17/222,242, filed Apr. 5, 2021.

Response to Office Action dated Mar. 11, 2025, U.S. Appl. No. 17/701,132, filed Mar. 22, 2022.

U.S. Appl. No. 17/701,132, filed Mar. 22, 2022.

Communication under Rule 71(3) EPC dated Oct. 4, 2024, European Patent Application No. 22155857.0-1122.

Notice of Allowance dated Jun. 18, 2025, U.S. Appl. No. 17/701,132, filed Mar. 22, 2022.

Response to Office Action dated Aug. 1, 2023, U.S. Appl. No. 17/222,242, filed Apr. 5, 2021.

Restriction Requirement dated Sep. 30, 2024, U.S. Appl. No. 17/701,132, filed Mar. 22, 2022.

Response to Restriction dated Oct. 3, 2024, U.S. Appl. No. 17/701,132, filed Mar. 22, 2022.

Extended European Search Report dated Jul. 18, 2022, European Patent Application No. 22155857.0-1126.

Restriction Requirement dated Apr. 10, 2023, U.S. Appl. No. 17/222,242, filed Apr. 5, 2021.

Response to Restriction dated Apr. 13, 2023, U.S. Appl. No. 17/222,242, filed Apr. 5, 2021.

Non-final Office Action dated May 23, 2023, U.S. Appl. No. 17/222,279.

\* cited by examiner 712 (e.g., 104 or 106)

722

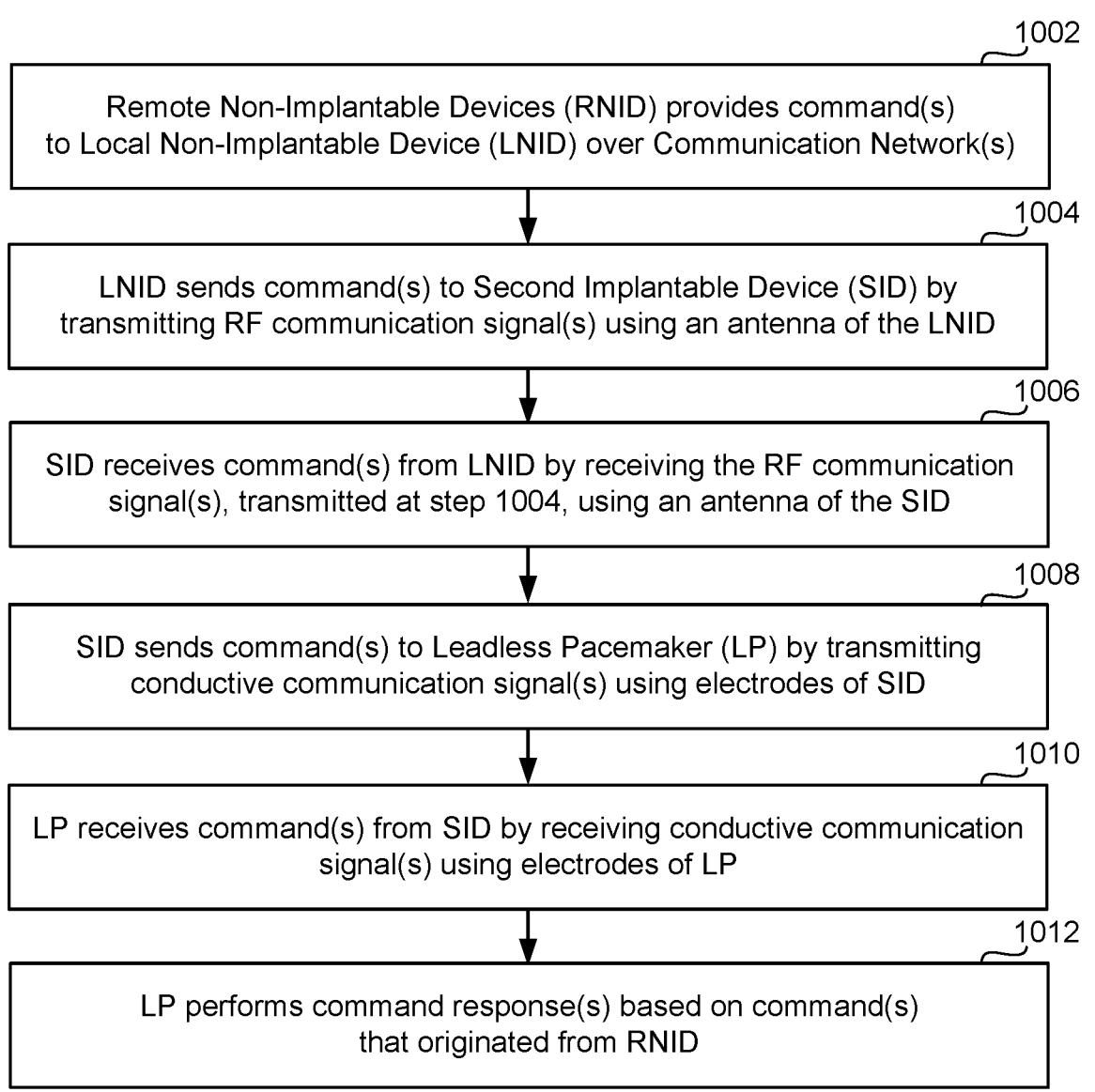

1002

Remote Non-Implantable Devices (RNID) provides command(s)
to Local Non-Implantable Device (LNID) over Communication Network(s)

1004

LNID sends command(s) to Second Implantable Device (SID) by
transmitting RF communication signal(s) using an antenna of the LNID

1006

SID receives command(s) from LNID by receiving the RF communication
signal(s), transmitted at step 1004, using an antenna of the SID

1008

SID sends command(s) to Leadless Pacemaker (LP) by transmitting
conductive communication signal(s) using electrodes of SID

1010

LP receives command(s) from SID by receiving conductive communication
signal(s) using electrodes of LP

1012

LP performs command response(s) based on command(s)
that originated from RNID

FIG. 10

SYSTEMS AND METHODS FOR REMOTE PROGRAMMING OF, AND OTHER FOLLOW-UP CAPABILITIES WITH, LEADLESS PACEMAKERS

PRIORITY CLAIM

This application is a continuation-in-part (CIP) of and claims priority to U.S. patent application Ser. No. 17/222,242, filed Apr. 5, 2021, issued as U.S. Pat. No. 11,918,817 on Mar. 5, 2024, which is incorporated herein by reference. This application also claims priority to U.S. Provisional Patent Application No. 63/243,601, filed Sep. 13, 2021, which is incorporated herein by reference.

FIELD OF TECHNOLOGY

Embodiments described herein generally relate to methods, systems and devices that can be used to provide remote programming of, and other follow-up capabilities and solutions for use with, one or more leadless pacemakers implanted within a patient.

BACKGROUND

An implantable medical device (IMD), such as a leadless pacemaker (LP), needs to communicate with a non-implanted device from time to time so that the non-implanted device can, e.g., program the implantable device, interrogate the implantable device, and/or obtain notifications and/or other types of diagnostic information from the implantable device. Typically, an LP is only capable of communicating with a non-implanted programmer that is operated by medical personnel, such as a physician or clinician. Accordingly, it is typically the case that an LP can only communicate with a non-implanted device when the patient visits a medical office that owns or otherwise has access to a non-implanted programmer, which can also be referred to an external programmer, or more succinctly as a programmer.

Communication between an LP and an external programmer may be facilitated by conductive communication via patient tissue, whereby at least two skin electrodes (that are part of or coupled to an external programmer) are attached to the skin of a patient within which (i.e., in whom) one or more LPs is/are implanted, and the skin electrodes are used to transmit information to and/or receive information from the LP(s) via conduction through body tissue of the patient. One potential problem with using conductive communication is that the orientation of the LP(s) can cause fading that can adversely affect both programmer-to-implant (p2i) communication and implant-to-programmer (i2p) communication. More specifically, certain orientations of an LP may cause conductive communication to be intermittent or stop completely, which may occur when an electric potential field generated between programmer skin electrodes has too small a difference between the electrodes of the LP. Another limitation of using conductive communication to provide communication between an LP and an external programmer is that the patient must be in physical contact with at least two skin electrodes. Despite its limitations, the use of conductive communication to facilitate communication between an external programmer on one or more LPs has proved to be practical and is often used.

In order for an LP to be interrogated by or otherwise communicate with an external programmer, a patient (within which the LP is implanted) needs to visit a medical facility that has an external programmer, as mentioned above. This is time consuming for both the patient and the medical personnel, as well as costly to the patient in terms of increasing their medical bills. Further, the COVID-19 pandemic has further shown the benefits of limiting in-person visits to hospitals and medical clinics. It would be beneficial if an LP can be interrogated from time to time without requiring the use of an external programmer located in close proximity to a patient and without requiring that a patient visit a medical facility.

SUMMARY

Certain embodiments of the present technology relate to methods, devices, and systems that enable a remote non-implantable device (RNID) to send commands to a leadless pacemaker (LP) implanted within a patient. Such commands can include an address or some other unique identifier of the LP, in order to indicate that the intended recipient of the commands is the particular LP. Certain such methods are for use with an LP configured to be implanted within a patient along with a second implantable device (SID) that is also configured to be implanted within the patient, a local non-implantable device (LNID) that is configured to communicate with the SID when the LNID is in close proximity to the patient within which the SID is implanted, and an RNID that is configured to communicate with the LNID. In accordance with certain such embodiments of the present technology, a method comprises the RNID providing one or more commands to the LNID over one or more communication networks. The method also comprises the LNID sending the one or more commands to the SID by transmitting one or more radio frequency (RF) communication signals, which include the one or more commands, using an antenna of the LNID. The method further comprises the SID receiving the one or more commands from the LNID by receiving the one or more RF communication signals, which include the one or more commands, using an antenna of the SID. The method also comprises the SID sending the one or more commands to the LP by transmitting one or more conductive communication signals, which include the one or more commands, using electrodes of the SID. Additionally, the method comprises the LP receiving the one or more commands from the SID by receiving the one or more conductive communication signals, which included the one or more commands, using electrodes of the LP. The method further comprises the LP performing one or more command responses based on the one or more commands that originated from the RNID. In accordance with certain embodiments, the one or more commands provided by the RNID may be translated and/or reformatted by at least one of the LNID or the SID before the one or more commands are received by the LP.

In accordance with certain embodiments, the SID acts as a communication gateway that converts RF communication signals to conductive communication signals and converts one or more data packets including the one or more commands from a first communication protocol that is used by the LNID to a second communication protocol that is used by the LP.

In accordance with certain embodiments, a method can also include the LNID changing a format of and/or performing a translation of the one or more commands that are received by the LNID from the RNID before the LNID sends the one or more commands to the SID. Additionally, or alternatively, the method can include the SID changing the format of and/or performing a translation of the one or more commands that are received by the SID from the LNID before the SID sends the one or more commands to the LP.

In accordance with certain embodiments, signals sent from the RNID to the LNID over one or more communication networks are encrypted, the one or more RF communication signals sent from the LNID to the SID are encrypted, and the one or more conductive communication signals sent from the SID to the LP are not encrypted.

In accordance with certain embodiments, the method further comprises establishing a secure communication session between the RNID and the LNID, prior to the RNID sending the one or more commands to the LNID, wherein the RNID sending the one or more commands to the LNID occurs during the secure communication session established between the RNID and the LNID. In other embodiments, the one or more conductive communication signals sent from the SID to the LP are also encrypted.

In accordance with certain embodiments, the method further comprises establishing a communication session between the RNID and the LP during which the LP sends one or more acknowledgment messages to the RNID in response to the LP successfully receiving the one or more commands that originated from the RNID. In certain such embodiments, the LP sending the one or more acknowledgement messages comprises: the LP sending the one or more acknowledgment messages to the SID by transmitting one or more further conductive communication signals, which include the one or more acknowledgement messages, using the electrodes of the LP; the SID receiving the one or more acknowledgment messages from the LP by receiving the one or more further conductive communication signals, which include the one or more acknowledgement messages, using the electrodes of the SID; the SID sending the one or more acknowledgment messages to the LNID by transmitting one or more further RF communication signals, which include the one or more acknowledgement messages, using the antenna of the SID; the LNID receiving the one or more acknowledgement messages from the SID by receiving the one or more further RF communication signals, which include the acknowledgement messages, using the antenna of the LNID; and the LNID providing the one or more acknowledgment messages to the RNID over one or more communication networks.

In accordance with certain embodiments, the SID comprises one of an insertable cardiac monitor (ICM), or a non-vascular implantable cardiac defibrillator (NV-ICD), but is not limited thereto. In accordance with certain embodiments, the LNID comprises one of a smart phone, a smart watch, a smart home hub, a tablet computer, a laptop computer, or a bedside monitor. The antenna of the LNID enables the LNID to transmit RF communication signals to, and receive RF communication signals from, the SID. At least one of an antenna of the LNID or a network interface of the LNID enables the LNID to communicate with the RNID over one or more communication networks.

In accordance with certain embodiments, the method further comprises the LP providing diagnostic information to the RNID, wherein the diagnostic information relates to at least one of the LP or a patient within which the LP is implanted. In certain such embodiments, the LP providing diagnostic information to the RNID comprises: the LP sending the diagnostic information to the SID by transmitting one or more further conductive communication signals using the electrodes of the LP; the SID receiving the diagnostic information from the LP by receiving the one or more further conductive communication signals using the electrodes of the SID; the SID sending the diagnostic information to the LNID by transmitting one or more further RF communication signals using the antenna of the SID; the LNID receiving the diagnostic information from the SID by receiving the one or more further RF communication signals using the antenna of the LNID; and the LNID sending the diagnostic information to the RNID by transmitting the diagnostic information over one or more communication networks.

Certain embodiments of the present technology are directed to a system including an LP, an SID, an LNID, and an RNID. The LP, which is configured to be implanted within a patient, includes electrodes used for sensing cardiac electrical activity, delivering pacing pulses, and performing conductive communication. The SID, which is also configured to be implanted within a patient, includes electrodes that are used for performing conductive communication with the LP, and also includes an antenna that enables the SID to communication with one or more non-implanted devices. The LNID, which is configured to communicate with the SID when the LNID is in close proximity to a patient within which the SID is implanted, includes an antenna that enables the LNID to send RF communication signals to, and receive RF communication signals from, the SID. The RNID is configured to communicate with the LNID over one or more communication networks. In accordance with certain embodiments, the RNID is configured to send one or more commands, that are intended for the LP, by transmitting the one or more commands to the LNID. The one or more commands that are received by the LNID, from the RNID, are sent as RF communication signals from the LNID to the SID using the antenna of the LNID. The one or more commands that are received by the SID from the LNID, are sent as conductive communication signals from the SID to the LP using the electrodes of the SID. The LP receives the one or more commands from the SID (which commands originated from the RNID) as conductive communication signals that are received using electrodes of the LP. In accordance with certain embodiments, the one or more commands that originated from the RNID may be translated and/or reformatted by at least one of the LNID or the SID before the one or more commands are received by the LP.

In accordance with certain embodiments, the SID is configured to act as a communication gateway that converts RF communication signals to conductive communication signals and converts one or more data packets including the one or more commands from a first communication protocol that is used by the LNID to a second communication protocol that is used by the LP.

In accordance with certain embodiments, the LNID is configured to change a format of and/or perform a translation of the one or more commands that the LNID receives from the RNID, before the LNID sends the one or more commands to the SID. Additionally, or alternatively, the SID is configured to change the format of and/or perform a translation of the one or more commands that the SID receives from the LNID, before the SID sends the one or more commands to the LP.

In accordance with certain embodiments, the RNID is configured to encrypt the one or more RF communication signals sent from the RNID to the LNID and/or the LNID is configured to encrypt the one or more RF communication signals sent from the LNID to the SID. In certain such embodiments, the one or more conductive communication signals sent from the SID to the LP are not encrypted. Explained another way, the command(s) sent from the RNID to the LNID are encrypted, the command(s) send from the LNID to the SID are encrypted, and the command(s) sent from the SID to the LP are not encrypted.

Certain embodiments of the present technology are directed to a method for enabling an LP to be responsive to commands that originated from an RNID that is remotely located relative to a patient within which the LP is implanted, wherein the LP is configured to communicate using conductive communication, and the RNID is not configured to communicate using conductive communication. Alternatively, the RNID may have conductive communication capabilities, but may not be able to perform conductive communication with the LP because the RNID is remotely located relative to a patient within which the LP is implanted. As used herein, the phrase "remotely located relative to" means in at least a different room. In certain embodiments, this phrase means in at least a different building, and in other specific embodiments means at least one mile away. In accordance with certain embodiments, such a method includes an SID receiving commands from a LNID, by receiving one or more RF communication signals, which include the commands, using an antenna of the SID, wherein the commands that the SID receives from the LNID originated from the RNID. The method also includes the SID sending the commands to the LP by transmitting conductive communication signals, which include the commands, using electrodes of the SID.

In accordance with certain embodiments, the method further comprises: the LP receiving the commands from the SID by receiving the conductive communication signals, which include the commands, using electrodes of the LP; and the LP performing command responses based on the commands that originated from the RNID. In certain such embodiments, the SID comprises one of an ICM or a NV-ICD, but is not limited thereto. In certain such embodiments, the LNID comprises one of a smart phone, a smart watch, a smart home hub, a tablet computer, a laptop computer, or a bedside monitor, and the antenna of the LNID enables the LNID to transmit RF communication signals to, and receive RF communication signals from, the SID.

In accordance with certain embodiments, the method includes the SID changing a format of and/or performing a translation of the commands that the SID receives from the LNID, before the SID sends the commands to the LP. In accordance with certain embodiments, the RF communication signals including the commands, which are received by SID from the LNID, are encrypted. In certain such embodiments, the conductive communication signals including the commands, which are sent from the SID to the LP, are not encrypted.

In accordance with certain embodiments, the method further comprises the SID receiving diagnostic information from the LP, and sending the diagnostic information to the LNID so that the LNID can forward the diagnostic information to the RNID over one or more communication networks.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views:

FIG. 10 is a high level flow diagram that is used to describe certain embodiments of the present technology that enable an RNID to program, and more generally send commands to, an LP.

DETAILED DESCRIPTION

Certain embodiments of the present technology relate to methods, systems and devices that can be used to provide remote follow-up solutions and capabilities for use with one or more leadless cardiac pacemakers implanted within a patient. More specifically, in accordance with certain embodiments of the present technology, a remote non-implanted device is used to send commands to a leadless cardiac pacemaker, wherein such commands can include one or more programming instructions, one or more measurement requests, one or more diagnostics updates, or combinations thereof, but are not limited thereto. Before providing addition details of the specific embodiments of the present technology mentioned above, an example environment in which embodiments of the present technology can be useful will first be described with reference to FIGS. 1-3. More specifically, FIGS. 1-3 will be used to describe an example cardiac pacing system, wherein pacing and sensing operations can be performed by multiple medical devices, which may include one or more leadless cardiac pacemakers, an implantable cardioverter defibrillator (ICD), such as a non-vascular ICD (NV-ICD), an implantable cardiac monitor (ICM) and/or a programmer to reliably and safely coordinate pacing and/or sensing operations. A leadless cardiac pacemaker can also be referred to more succinctly herein as a leadless pacemaker (LP).

Figure 1:
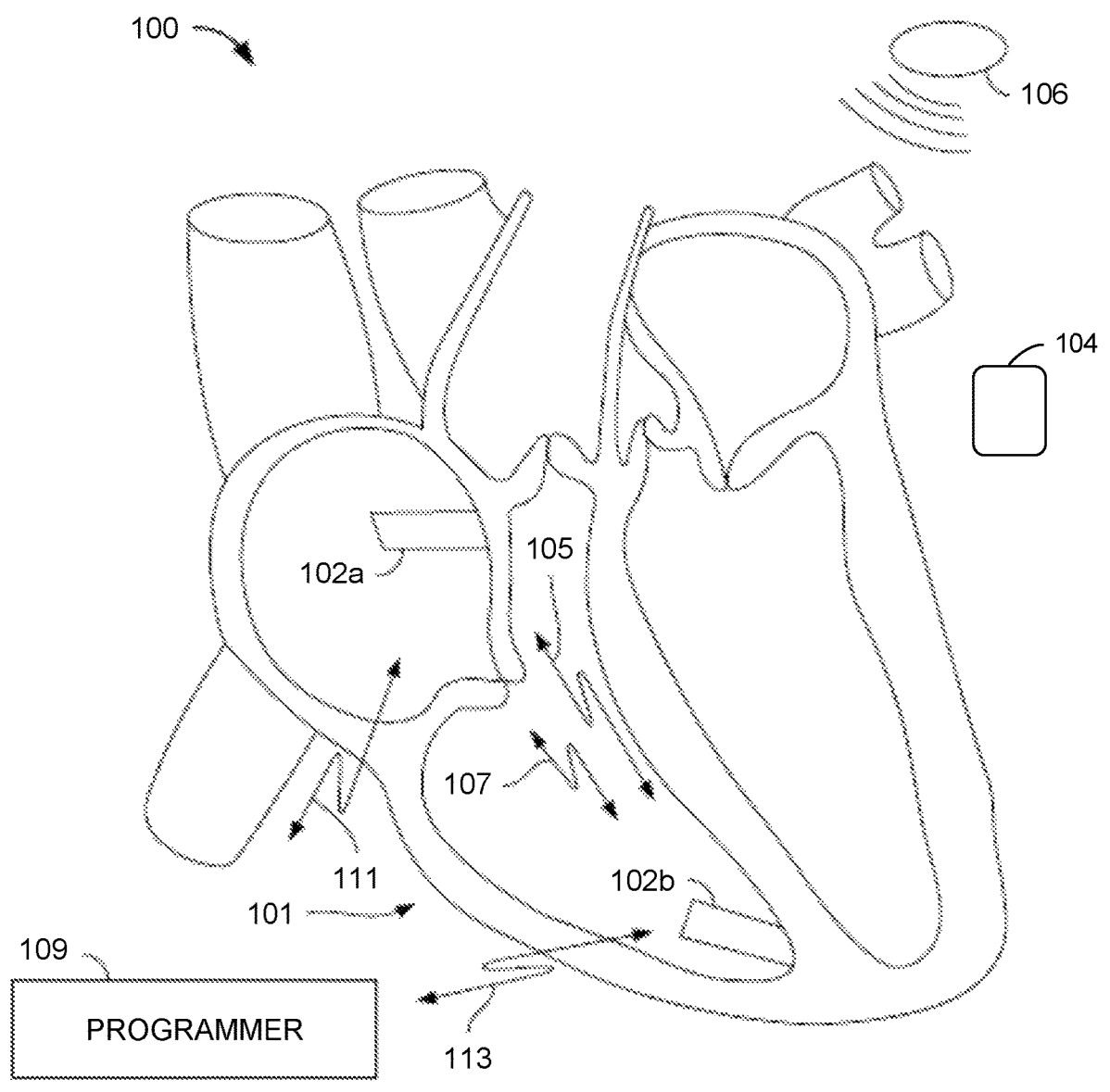
FIG. 1 illustrates a system that includes a plurality of implantable devices that are implanted in a patent and an external programmer that can be used to program and/ otherwise communicate with the implantable devices.

FIG. 1 illustrates a system 100 that is configured to be implanted in a heart 101. The system 100 includes LPs 102a and 102b located in different chambers of the heart 101. LP 102a is located in a right atrium, while LP 102b is located in a right ventricle. LPs 102a and 102b communicate with one another to inform one another of various local physiologic activities, such as local intrinsic events, local paced events, and/or the like. LPs 102a and 102b may be constructed in a similar manner, but operate differently based upon which chamber LP 102a or 102b is located. The LPs 102a and 102b may sometimes be referred to collectively herein as the LPs 102, or individually as an LP 102.

In certain embodiments, LPs 102a and 102b communicate with one another, and/or with an ICM 104, and/or with an ICD 106, by conductive communication through the same electrodes that are used for sensing and/or delivery of pacing therapy. In such embodiments, the ICM 104 and/or the ICD 106 are examples of a second implantable device (SID), which is discussed below in more detail with reference to FIGS. 7, 8 and 10. The LPs 102a and 102b may also be able to use conductive communication to communicate with a non-implanted device, e.g., an external programmer 109, having electrodes placed on the skin of a patient within which the LPs 102a and 102b are implanted. While not shown (and not preferred, since it would increase the size and power consumption of the LPs 102a and 102b), the LPs 102a and 102b can potentially include an antenna and/or telemetry coil that would enable them to communicate with one another, the ICD 106 and/or a non-implanted device using RF or inductive communication. While only two LPs are shown in FIG. 1, it is possible that more than two LPs can be implanted in a patient. For example, to provide for bi-ventricular pacing and/or cardiac resynchronization therapy (CRT), in addition to having LPs implanted in or on the right atrial (RA) chamber and the right ventricular (RV) chamber, a further LP can be implanted in or on the left ventricular (LV) chamber. It is also possible that a single LP be implanted within a patient, e.g., in or on the RV chamber, the RA chamber, or the LV chamber, but not limited thereto.

In some embodiments, one or more LP 102a, 102b can be co-implanted with the ICM 104 and/or the ICD 106. In such embodiments, the ICM 104 and/or ICD 106 are examples of a second implantable device (SID), which is discussed below in more detail with reference to FIGS. 7, 8 and 10, as noted above. Each LP 102a, 102b uses two or more electrodes located within, on, or within a few centimeters of the housing of the pacemaker, for pacing and sensing at the cardiac chamber, for bidirectional conductive communication with one another, with the programmer 109, the ICD 106, and/or the ICM 104. Such an ICM 104 can be intended for subcutaneous implantation at a site near the heart 101. The ICM 104 can include, for example, a pair of spaced-apart sense electrodes positioned with respect to a housing, wherein the sense electrodes provide for detection of far-field EGM signals, and can also be used for conductive communication with one or more other implanted devices, such as the LP(s) 102a and/or 102b and/or the ICD 106. Such an ICM can also include an antenna that is configured to wirelessly communicate with an external device, such as an external programmer 109, or a local non-implantable device (LNID) (e.g., 722 described below with reference to FIGS. 7, 9 and 10), in accordance with one or more wireless communication protocols (e.g., Bluetooth, Bluetooth low energy, Wi-Fi, etc.). The housing of the ICM can include various other components such as: sense electronics for receiving signals from the electrodes, a microprocessor for processing the signals in accordance with algorithms, a loop memory for temporary storage of cardiac activity (CA) data, a device memory for long-term storage of CA data upon certain triggering events, sensors for detecting patient activity and a battery for powering components.

In accordance with certain embodiments of the present technology, the ICM 104 can act as a gateway communication device between the LPs 102a and/or 102b and an external programmer 109 and/or a remote monitor, as will be described in additional detail below. As will be described in additional detail below, instead of the ICM 104 acting as a gateway communication device between the LPs 102a and/or 102b and an external device, the ICD 106 can instead act as the gateway. It is also within the scope of the embodiments described herein that some other implantable device, which may not have any monitoring or therapeutic capabilities, acts as the communication gateway.

Figure 2:
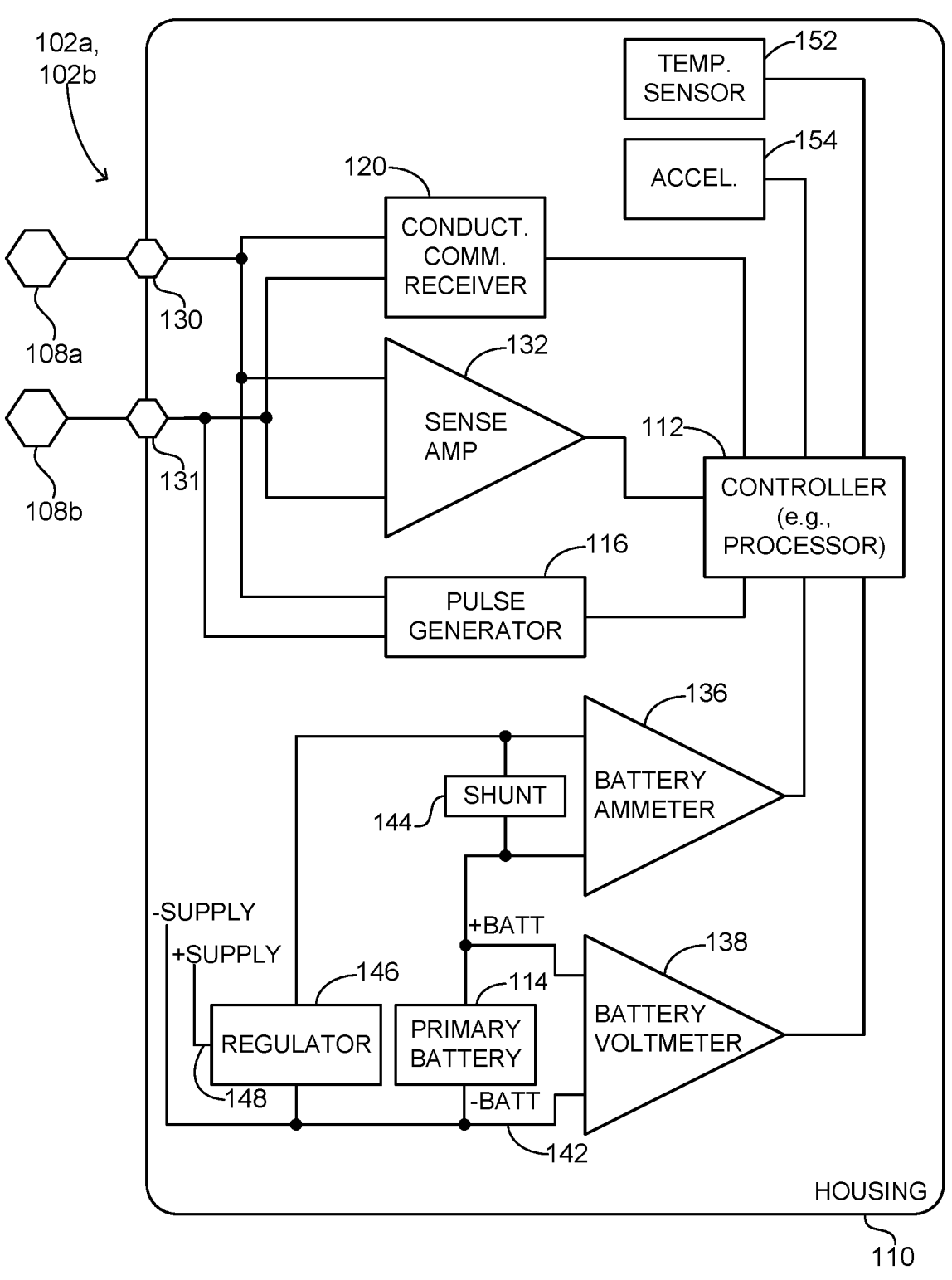
FIG. 2 is a block diagram of a single LP in accordance with certain embodiments herein.

Referring to FIG. 2, a block diagram shows an example embodiment for portions of the electronics within LPs 102a, 102b configured to provide conductive communication through the same electrodes that are used for cardiac pacing and/or sensing. Each of the LPs 102a, 102b includes at least two leadless electrodes configured for delivering cardiac pacing pulses, sensing evoked and/or natural cardiac electrical signals, and uni-directional and/or bi-directional communication. In FIG. 2 (and FIG. 3) the two electrodes shown therein are labeled 108a and 108b. Such electrodes can be referred to collectively as the electrodes 108, or individually as an electrode 108. An LP 102, or other type of IMD, can include more than two electrodes, depending upon implementation.

In FIG. 2, each of the LPs 102a, 102b is shown as including a conductive communication receiver 120 that is coupled to the electrodes 108 and configured to receive conductive communication signals from the other LP 102 and/or the ICD 104, but not limited thereto. The conductive communication receiver 120. Although one receiver 120 is depicted in FIG. 2, in other embodiments, each LP 102a, 102b may only include one or more additional receivers. O As will be described in additional detail below, the pulse generator 116 can function as a transmitter that transmits conductive communication signals using the electrodes 108. In certain embodiments, LPs 102a and 102b may communicate over more than just first and second communication channels 105 and 107. In certain embodiments, LPs 102a and 102b may communicate over one common communication channel 105. More specifically, LPs 102a and 102b can communicate conductively over a common physical channel via the same electrodes 108 that are also used to deliver pacing pulses. Usage of the electrodes 108 for communication enables the one or more LPs 102a, 102b to perform antenna-less and telemetry coil-less communication. Where to implantable devices (such as to LPs 102a and 102b) communicate with one another using conductive communication, such conductive communication can be referred to as implant-to-implant (i2i) communication.

Optionally, the LP (or other IMD) that receives any conductive communication signal from another LP (or other IMD) or from a non-implanted device (e.g., a programmer 109) may transmit a receive acknowledgement indicating that the receiving LP (or other IMD, or non-implanted device) received the conductive communication signal. In certain embodiments, where an IMD expects to receive a conductive communication signal within a window, and fails to receive the conductive communication signal within the window, the IMD may transmit a failure-to-receive acknowledgement indicating that the receiving IMD failed to receive the conductive communication signal. Other variations are also possible and within the scope of the embodiments described herein. Each conductive communication signal can include one or more sequences of conductive communication pulses. In accordance with certain embodiments, conductive communication pulses are delivered during cardiac refractory periods that are identified or detected by the LP(s) and/or other IMD(s). In accordance with certain embodiments, conductive communication pulses are sub-threshold, i.e., they are below the capture threshold for the patient.

The event messages enable the LPs 102a, 102b to deliver synchronized therapy and additional supportive features (e.g., measurements, etc.). To maintain synchronous therapy, each of the LPs 102a and 102b is made aware (through the event messages) when an event occurs in the chamber containing the other LP 102a, 102b. Some embodiments described herein provide efficient and reliable processes to maintain synchronization between LPs 102a and 102b without maintaining continuous communication between LPs 102a and 102b. In accordance with certain embodiments herein, low power event messages/signaling may be maintained between LPs 102a and 102b synchronously or asynchronously. Additional details of i2i event messages that are sent between LPs 102 are provided in U.S. patent application Ser. No. 17/222,242, which was incorporated herein by reference above.

For synchronous event signaling, LPs 102a and 102b may maintain synchronization and regularly communicate at a specific interval. Synchronous event signaling allows the transmitter and receivers in each LP 102a,102b to use limited (or minimal) power as each LP 102a, 102b is only powered for a small fraction of the time in connection with transmission and reception. For example, LP 102a, 102b may transmit/receive (Tx/Rx) communication messages in time slots having duration of 10-20 μs, where the Tx/Rx time slots occur periodically (e.g., every 10-20 ms). Such time slots can also be referred to as windows.

During asynchronous event signaling, LPs 102a and 102b do not maintain communication synchronization. During asynchronous event signaling, one or more of receivers 120 and 122 of LPs 102a and 102b may be "always on" (always awake) to search for incoming transmissions. However, maintaining LP receivers 120, 122 in an "always on" (always awake) state presents challenges as the received signal level often is low due to high channel attenuation caused by the patient's anatomy. Further, maintaining the receivers awake will deplete the battery 114 more quickly than may be desirable.

To overcome the foregoing receive power limit, a pulsed transmission scheme may be utilized in which communication transmissions occur correlated with an event. By way of example, the pulsed transmission scheme may be simplified such that each transmission constitutes a single pulse of a select amplitude and width.

Still referring to FIG. 2, each LP 102a, 102b is shown as including a controller 112 and a pulse generator 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies. The controller 112 and the pulse generator 116 may be configured to transmit event messages, via the electrodes 108, in a manner that does not inadvertently capture the heart in the chamber where LP 102a, 102b is located, such as when the associated chamber is not in a refractory state. In addition, a LP 102a, 102b that receives an event message may enter an "event refractory" state (or event blanking state) following receipt of the event message. The event refractory/blanking state may be set to extend for a determined period of time after receipt of an event message in order to avoid the receiving LP 102a, 102b from inadvertently sensing another signal as an event message that might otherwise cause retriggering. For example, the receiving LP 102a, 102b may detect a measurement pulse from another LP 102a, 102b or programmer 109.

In accordance with certain embodiments herein, programmer 109 may communicate over a programmer-to-LP channel, with LP 102a, 102b utilizing the same communication scheme. The external programmer 109 may listen to the event message transmitted between LP 102a, 102b and synchronize programmer to implant communication such that programmer 109 does not transmit communication signals 113 until after an implant to implant messaging sequence is completed.

In accordance with certain embodiments, LP 102a, 102b may combine transmit operations with therapy. The transmit event marker may be configured to have similar characteristics in amplitude and pulse-width to a pacing pulse and LP 102a, 102b may use the energy in the event messages to help capture the heart. For example, a pacing pulse may normally be delivered with pacing parameters of 2.5V amplitude, 500 ohm impedance, 60 bpm pacing rate, 0.4 ms pulse-width. The foregoing pacing parameters correspond to a current draw of about 1.9 μA. The same LP 102a, 102b may implement an event message utilizing event signaling parameters for amplitude, pulse-width, pulse rate, etc. that correspond to a current draw of approximately 0.5 μA for transmit. LP 102a, 102b may combine the event message transmissions with pacing pulses. For example, LP 102a, 102b may use a 50 μs wakeup transmit pulse having an amplitude of 2.5V which would draw 250 nC (nano Coulombs) for an electrode load of 500 ohm. Additional details of how the LPs 102 may combine the event message transmissions with pacing pulses are provided in U.S. patent application Ser. No. 17/222,242, which was incorporated herein by reference above.

In some embodiments, the individual LP 102a can comprise a hermetic housing 110 configured for placement on or attachment to the inside or outside of a cardiac chamber and at least two leadless electrodes 108 proximal to the housing 110 and configured for conductive communication with at least one other device within or outside the body. Depending upon the specific implementation, and/or the other device with which an LP is communicating, the conductive communication may be unidirectional or bidirectional.

FIG. 2 depicts a single LP 102a (or 102b) and shows the LP's functional elements substantially enclosed in a hermetic housing 110. The LP 102a (or 102b) has at least two electrodes 108 located within, on, or near the housing 110, for delivering pacing pulses to and sensing electrical activity from the muscle of the cardiac chamber, and for conductive communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receivers 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

The electrodes 108 can be configured to communicate bidirectionally among the multiple leadless cardiac pacemakers, the implanted ICD 106 and/or the implanted ICM 104 to coordinate pacing pulse delivery and optionally other therapeutic or diagnostic features using messages that identify an event at an individual pacemaker originating the message and a pacemaker receiving the message react as directed by the message depending on the origin of the message. An LP 102a, 102b that receives the event message reacts as directed by the event message depending on the message origin or location. In some embodiments or conditions, the two or more leadless electrodes 108 can be configured to communicate bidirectionally among the one or more LPs, the ICD 106, and/or the ICM 104 and transmit data including designated codes for events detected or created by an individual pacemaker. Individual pacemakers can be configured to issue a unique code corresponding to an event type and a location of the sending pacemaker.

In some embodiments, an individual LP 102a, 102b can be configured to deliver a pacing pulse with an event message encoded therein, with a code assigned according to pacemaker location and configured to transmit a message to one or more other leadless cardiac pacemakers via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 102b may receive and relay an event message from LP 102a to an external programmer. Similarly, information communicated on the outgoing channel can also include a message to another leadless cardiac pacemaker or pacemakers, or to the ICD or ICM, that the sending leadless cardiac pacemaker has sensed a heartbeat or has delivered a pacing pulse at the location of the sending pacemaker.

Referring again to FIGS. 1 and 2, the system 100 may comprise an ICD 106 and/or ICM 104 in addition to one or more LPs 102a, 102b configured for implantation in electrical contact with a cardiac chamber and for performing cardiac rhythm management functions in combination with the implantable ICD 106 and/or the ICM 104. The implantable ICD 106 and/or ICM 104 and the one or more LPs 102a, 102b configured for leadless intercommunication by information conduction through body tissue and/or wireless transmission between transmitters and receivers in accordance with the discussed herein.

As shown in the illustrative embodiments, each LP pacemaker 102a, 102b can comprise two or more leadless electrodes 108 configured for delivering cardiac pacing pulses, sensing evoked and/or natural cardiac electrical signals, and bidirectionally communicating with one another and/or the co-implanted ICD 106.

Also shown in FIG. 2, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the controller 112 with an indication of battery current drain and indirectly of device health. The illustrative power supply can be a primary battery 114.

Referring to FIG. 2, the LP is shown as including a temperature sensor 152. The temperature sensor can be any one of various different types of well-known temperature sensors, or can be a future developed temperature sensor. The temperature sensor 152 can be used in various manners. For example, the temperature sensor 152 can be used to detect an activity level of the patient to adjust a pacing rate, i.e., for use in rate responsive pacing. Accordingly, the controller 112 can be configured to detect an activity level of a patient based on core blood temperature measurements obtained using the temperature sensor 152.

Referring to FIG. 2, the LP is also shown as including an accelerometer 154 which can be hermetically contained within the housing 110. The accelerometer 154 can be any one of various different types of well-known accelerometers, or can be a future developed accelerometer. The accelerometer 154 can be used to detect an activity level of the patient to adjust a pacing rate, i.e., for use in rate responsive pacing. It would also be possible to use outputs of both the accelerometer 154 and the temperature sensor 152 to monitor the activity level of a patient. Alternatively, or additionally, a patient's activity level can be monitored based on their heart rate, as detected from an (electrogram) EGM sensed using the electrodes 108, and/or sensed using a plethysmography signal obtained using a plethysmography sensor (not shown) or a heart sound sensor (not shown), but not limited thereto.

In various embodiments, LP 102a, 102b can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one LP 102 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

Figure 3:
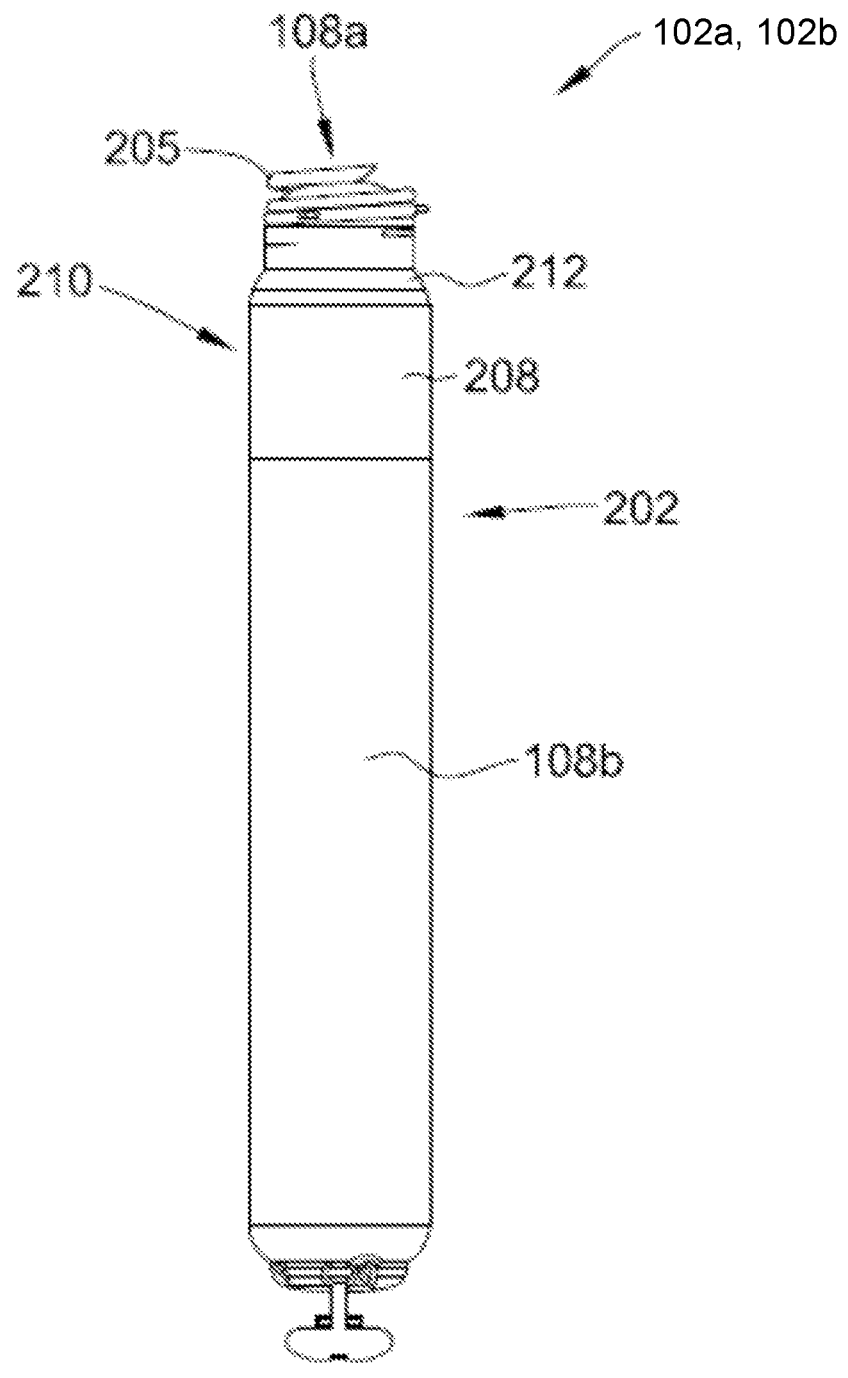
FIG. 3 illustrates an LP in accordance with certain embodiments herein.

FIG. 3 shows an example form factor of an LP 102a, 102b. The LP can include a hermetic housing 202 (110) with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. The electrodes 108a and 108b are examples of the electrodes 108 shown in and discussed above with reference to FIG. 2.

The housing can also include an electronics compartment 210 within the housing that contains the electronic components necessary for operation of the pacemaker, including, e.g., a pulse generator, receiver, a battery, and a processor for operation. The hermetic housing 202 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 3, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 3, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art. The term metal, as used herein, also encompasses alloys that are electrically conductive.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 3, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 2) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

Conductive Communication Between an LP and External Programmer

Figures 4, 5:
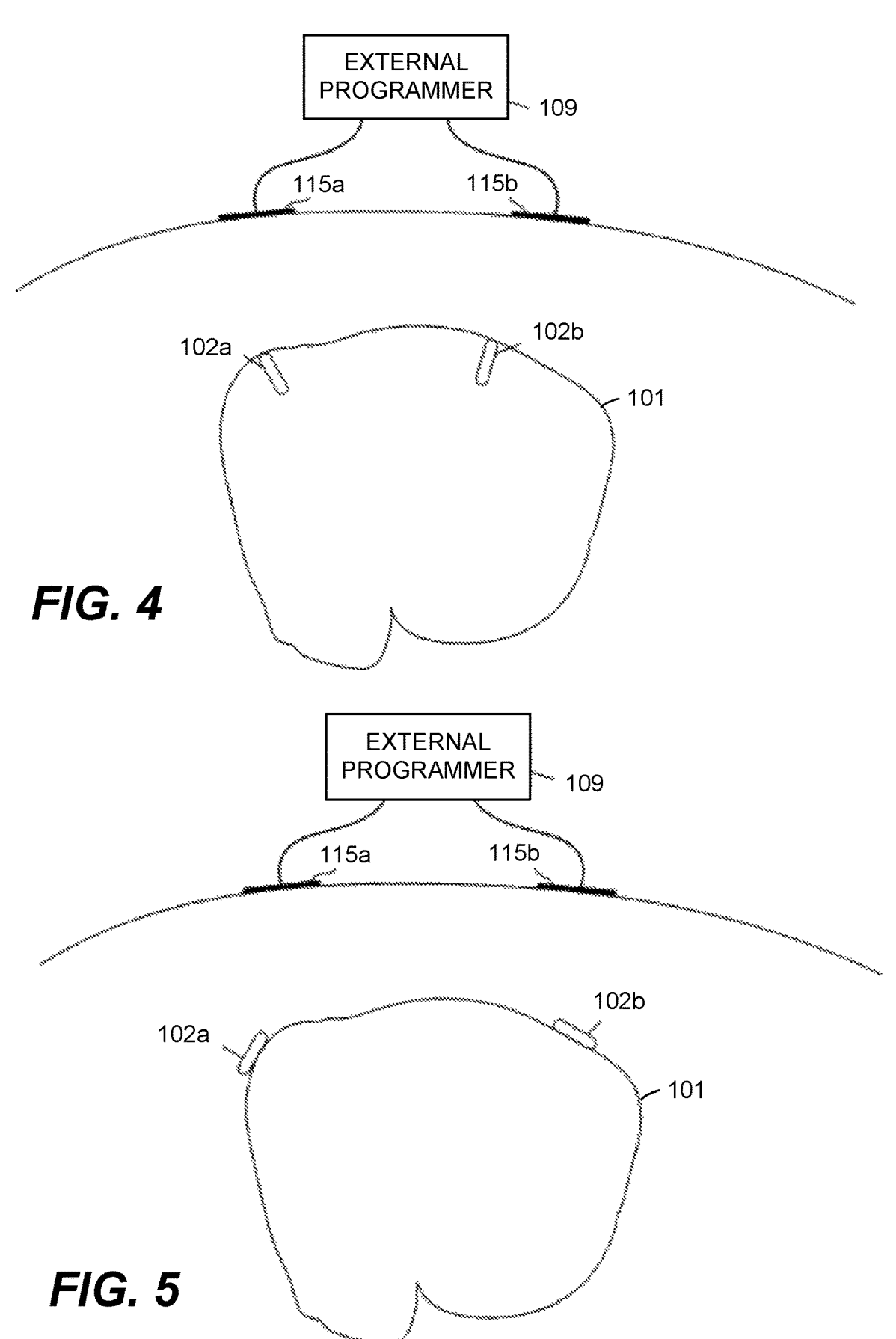
FIG. 4 depicts a sample configuration involving an external programmer and two endocardially implanted LPs.
FIG. 5 depicts a sample configuration involving an external programmer and two LPs implanted epicardially (on the external heart surface).

FIGS. 4 and 5 are schematic pictorial views depicting how an external programmer coupled to skin electrodes 115a, 115b can communicate with the LP 102a and/or the LP 102b via conductive communication, which is also referred to interchangeably herein as conducted communication. Such communication may take place via bidirectional communication pathways comprising a receiving pathway that decodes information encoded on pulses generated by one or more of the LPs 102a or 102b and conductive through body tissue to the external programmer 109. According to the illustrative arrangement, the bidirectional communication pathways can be configured for communication with multiple LPs 102a and 102b via two or more electrodes and conduction through body tissue.

In accordance with certain embodiments, the external programmer 109 is connected by a communication transmission channel and has transmitting and receiving functional elements for a bidirectional exchange of information with one or more IMDs, such as LP 102a and/or LP 102b. The communication channel includes two or more programmer skin electrodes which can be affixed or secured to the surface of the skin. From the point of the skin, the communication transmission channel is wireless, includes the ion medium of the intra- and extra-cellular body liquids, and enables electrolytic-galvanic coupling between the programmer skin electrodes, which can also be referred to as surface electrodes, and the LPs, or more generally, IMDs. The bidirectional communication pathways can further comprise a transmitting pathway that passes information from the external programmer 109 to one or more of the LPs 102a and/or 102b by direct conduction through the body tissue by modulation that avoids skeletal muscle stimulation using modulated signals at a frequency in a range from approximately 10 kHz to 100 kHz, or at higher frequencies. For example, p2i communication signals may be transmitted at a center frequency (fc) of 500 kHz.

Information transmitted from the external programmer 109 to the implanted LPs is conveyed by modulated signals at the approximate range of 10 kHz to 100 kHz which is a medium-high frequency, or at higher frequencies. The signals are passed through the communication transmission channel by direct conduction. A modulated signal in the frequency range has a sufficiently high frequency to avoid any depolarization within the living body which would lead to activation of the skeletal muscles and discomfort to the patient. The frequency is also low enough to avoid causing problems with radiation, crosstalk, and excessive attenuation by body tissue. Thus, information may be communicated at any time, without regard to the heart cycle or other bodily processes. No restriction is imposed regarding location of electrode placement on the body because low signal attenuation enables the signal to travel throughout the body and to be received by the LPs 102a and 102b.

FIG. 4 depicts a sample configuration involving the external programmer 109 and two endocardially implanted LPs 102a and 102b. The external programmer 109 is physically connected to the skin surface via two programmer skin electrodes 115a and 115b (also referred to as surface electrodes), which can serve three functions. The programmer skin electrodes 115a and 115b can be referred to individually as a programmer skin electrode 115 (or a surface electrode 115), or collectively as programmer skin electrodes 115 (or surface electrodes 115). First, the electrodes 115 can be used transmit encoded information from the programmer 109 to the LPs or other IMD(s) using a modulated signal, e.g., at a medium frequency 10 kHz to 100 kHz. Second, the programmer skin electrodes 115 can be used to receive information from individual LPs or other IMD(s) by detecting encoded information in the pacing pulses of the LP(s). Third, the programmer skin electrodes 115 can receive or sense a surface electrocardiogram for display and analysis by the programmer 109.

In FIG. 4, the two LPs 102a and 102b are implanted within the heart 101 endocardially. Alternatively, as shown in FIG. 5, the two LPs 102a and 102b can be implanted by affixing to the exterior surface of the heart 101. The programmer skin electrodes 115 and the external programmer 109 function similarly in arrangements shown in FIGS. 4 and 5 whether the LPs 102a and 102b are implanted endocardially or epicardially (on the external heart surface). No restriction is imposed that the LPs are all implanted inside or all implanted outside the heart. One or more may be implanted endocardially along with others implanted on the outer surface of the heart. The functioning of the programmer 109 is substantially the same. Although two programmer skin electrodes 115 are shown in FIGS. 4 and 5, two is generally the minimum number of programmer skin electrodes required for adequate conductive communication. More programmer skin electrodes 115 can be used, enabling an ECG to be sensed at multiple vectors for better analysis. More than two programmer skin electrodes may also enable a choice of vectors for conductive communication with the LPs, thereby maximizing the signal to noise ratio of the system. FIGS. 4 and 5 each depict two LPs 102a and 102b. One, two, or more LPs 102 can be implanted, depending on the number of pacemakers appropriate for effective therapy.

In various embodiments, the external programmer 109 can be configured to perform one or more operations such as electrocardiogram sensing, retrieving status information from implanted pacemakers, modifying configuration parameters of multiple implanted pacemakers simultaneously in information passed through a common electrode set, displaying electrocardiograms, displaying information received from the at least one implantable device, and/or others.

In the embodiments described with reference to FIGS. 4 and 5, in order for an LP 102 to be programmed by, interrogated by or otherwise communicate with the non-implanted programmer 109, a patient (within which the LP(s) 102 is/are implanted) needs to visit a medical facility that has an external programmer 109, as mentioned above. This is time consuming for both the patient and the medical personnel, as well as costly to the patient in terms of increasing their medical bills. Further, the COVID-19 pandemic has further shown the benefits of limiting in-person visits to hospitals and medical clinics. Certain embodiments of the present technology, which are described below, enable an LP to be programmed and/or interrogated from time to time without requiring the use of an external programmer (e.g., 109) located in close proximity to a patient and without requiring that a patient visit a medical facility.

Figure 6:
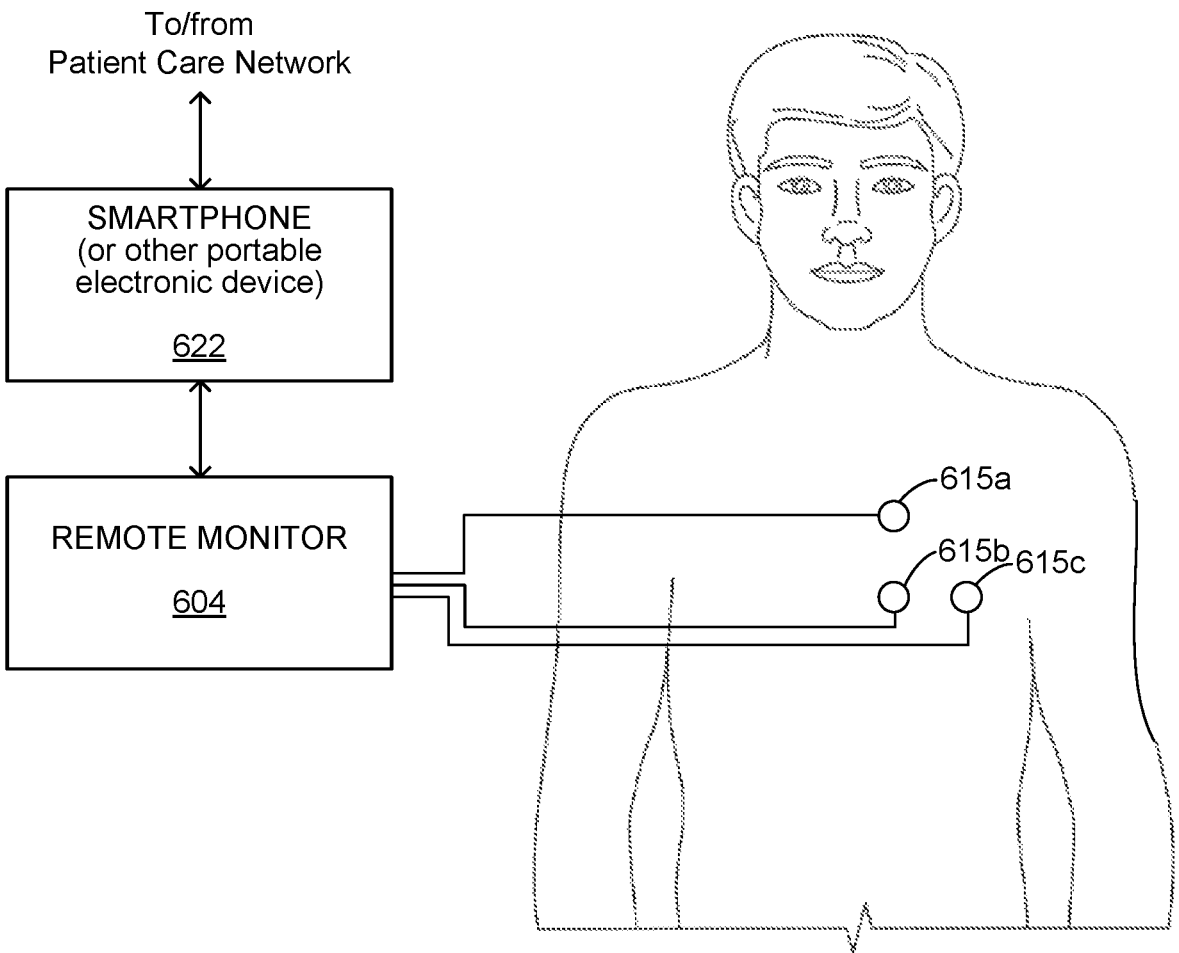
FIG. 6 is a high-level block diagram of an example remote follow-up system that includes electrodes that are in contact with a patient's skin and are connected to a remote monitor device.

FIG. 6 is a high-level block diagram of an example remote follow-up device or system includes electrodes 615a, 615b, 615c that are in contact with a patient's skin and are connected to a remote monitor device 604. The remote monitor device 604 can communicate directly with a patient care network if the remote minor device 604 has appropriate communication capabilities for doing so. Alternatively, the remote monitor device 604 can be communicatively coupled to a smartphone 622 via a wired or wireless connection, and the remote monitor device 604 can utilize the communication capabilities of the smartphone 622 (or tablet computing device or other portable electronic device with communication capabilities, such as a smart watch) to communicate with the patient care network. The electrodes 615a, 615b, and 615c can be separately attachable to a patient's chest, or they can be incorporated into a wearable vest or stick-on patch. Either way, the three electrodes 615a, 615b, 615c can provide for a pair of orthogonal sensing vectors. Alternatively, the system can include as few as two electrodes to provide for a single sensing vector. A software application can provide for a connection through the Internet to a patient care network, such as the Merlin.net system, where a physician can monitor key parameters of one or more LPs, therapy delivery and patient status. The hardware design for this system could utilize a smartphone (or tablet computing device or other portable electronic device) as both a power source and controller, with the monitor device providing the two-way communication (sensing and pulses) and hardware interface to the electrodes. In certain embodiment, the electrodes could utilize single use stick-on electrodes and then re-usable clips to connect to the device. The overall system can be used to compensate for the minimal on-board data storage included in LPs by obtaining EGM recordings as needed while worn. A stick-on patch or wearable vest can provide for conductive communication/telemetry through a programmer-to-implant (p2i) protocol, or the like. Since the electrodes can be attached to a patient for an extended period of time, without requiring constant attention or cooperation from the patient, the electrodes can allow for slower speed transmission of data, and can provide for real time recording of extended EGM data that would require too much memory to store within an LP's memory. While the embodiment described with reference to FIG. 6 may provide some benefits over the embodiments described above with reference to FIGS. 4 and 5, electrodes still need to be in contact with the skin of the patient in order for the LP to communicate with the remote patient care network, which is inconvenient and requires more patient compliance than desired. Environment that Enables an RNID to Send Commands to an LP Referring to FIG. 7, certain embodiments of the present technology, which are described below, are for use with a leadless pacemaker (LP) 702 configured to be implanted within a patient, a second implantable device (SID) 712 that is also configured to be implanted within the patient, a local non-implantable device (LNID) 722 that is configured to communicate with the SID 712 when the LNID is in close proximity to the patient within which the SID is implanted, and a remote non-implantable device (RNID) 732 that is configured to communicate with the LNID 722. The RNID 732 is remotely located relative to the patient in which the LP 702 is implanted, and thus, is remotely located relative to the LP 702. As used herein, the phrase "remotely located relative to" means in at least a different room. In certain embodiments, this phrase means in at least a different building, and in other specific embodiments means at least one mile away. Such embodiments can be used for enabling the RNID 732 to send one or more commands to the LP 702. Such commands can include, e.g., one or more programming instructions, one or more measurement requests, one or more diagnostics updates, or combinations thereof, but are not limited thereto. Accordingly, where the commands include one or more programming instructions, such embodiments enable programming of the LP 702 by the RNID 732, as explained in further detail below. Example details of the RNID 732 are described below with reference to FIG. 11. The RNID 732 can be part of a remote patient care network, but is not limited thereto.

Figure 7:
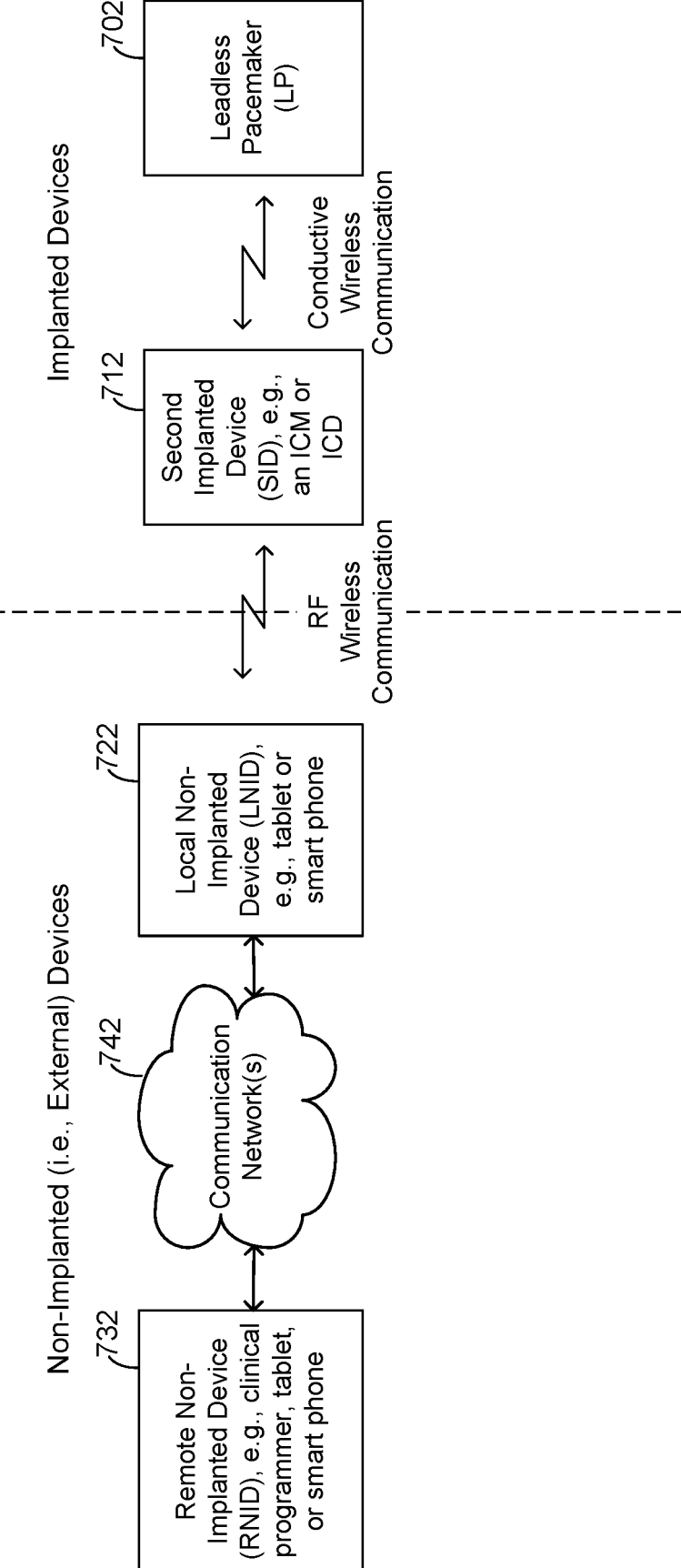
FIG. 7 is a high level block diagram that is used to describe how commands can be sent from a remote non-implantable device (RNID) to an LP, wherein the RNID is remotely located relative to the LP, in accordance with certain embodiments of the present technology.

The LP 702 can be, e.g., one of the LPs 102a or 102b. Accordingly, example details of the LP 702 were already described above with reference to FIGS. 1-3. In accordance with certain embodiments, the only way the LP 702 is able to communicate with another device, which may or may not be implanted, is using conductive communication. For example, while the LP 702 is configured to perform conductive communication, the LP 702 is not configured to perform RF communication, and is not configured to perform inductive communication. While only one LP 702 is shown in FIG. 7, one or more additional LPs can also be implanted within a patient and be used in the embodiments described herein. In certain embodiments, the LP 702 can enable transmission of a real time EGM signal (sensed using electrodes of the LP) to a physician through an SID, to a patient app on an LNID, and eventually to a physician's app on an RNID.

The SID 712 can be, e.g., the ICM 104 or the ICD 106. Alternatively, the SID 712 can be an implantable device that does not perform any type of therapy or physiologic monitoring, but rather, has the primary or sole function of acting as a communication gateway between the LP 702 and the LNID 722. In accordance with certain embodiments of the present technology, the SID 712 includes at least a pair of electrodes and is capable of performing conductive communication using its electrodes to thereby enable the SID 712 to communicate with the LP 702. Additionally, the SID 712 includes an antenna and is capable of performing RF communication using its antenna to thereby enable the SID 712 to wirelessly communicate with the LNID 722 that is in close proximity to (e.g., within about 15 feet of) the patient within which the SID 712 and LP 702 are implanted. Depending upon the specific embodiment, there are various different types of wireless communication technologies that can be used by the SID 712 to communicate with the LNID 722, and vice versa, such as, but not limited to, Bluetooth, Bluetooth Low Energy (BLE), WiFi, and Medical Device Radiocommunications Service (MedRadio). In other words, the RF communication signals transmitted between the SID 712 and the LNID 722 can be Bluetooth signals, BLE signals, WiFi signals, or MedRadio signals, but are not limited thereto. Example details of the SID 712 are described below with reference to FIG. 8. Example details of the LNID 722 are described below with reference to FIG. 9.

One technique for encoding information on communication pulses involves varying the timing between consecutive pulses in a pulse sequence. The interval between any two pulses can be varied slightly to impart information on the pulse series. The amount of information, in bits, is determined by the time resolution of the pulse shift. The steps of pulse shifting are generally on the order of microseconds. The method of encoding information in variation of pulses is less effective if many of the pulses are inhibited or triggered. Accordingly, a technique for conductive communication can comprise generating pulses on electrodes of an LP and encoding information onto generated pulses comprising selectively varying timing between consecutive pulses. Alternatively or in addition to encoding information in gated sections and/or pulse interval, overall pulse width can be used to encode information. Additionally, or alternatively, information encoding can be performed using on-off keying, amplitude modulation, frequency-shift keying, frequency modulation, or amplitude shift keying, but is not limited thereto. These are just a few examples, which are not intended to be all encompassing.

The LP(s) and/or other SID can encode and/or decode information using various techniques such as encoding the information using pulse width, binary-coded notches in a pulse, modulation of off-time between pacing pulses, or other suitable encoding techniques. An external programmer (e.g., 109, in FIGS. 1, 4 and 5) or another IMD, such as an LP or SID, can encode and/or decode information using on-off keying encoding and modulation techniques. However, any other appropriate method can be used whereby a modulated bit-stream can be generated at a medium high frequency, for example frequency-shift keying, frequency modulation, or amplitude shift keying. The conductive communication between an LP and an SID is an example of i2i communication.

From a communication gateway point of view, or more generally, a relay point of view, the SID 712 can function as a smart communication node or a dumb communication node. For example, where the SID 712 functions as a dumb node, the SID 712 can receive low level write and/or read commands originating from the RNID 732 (by way of the LNID 722), and just pass the write and/or read commands to the LP 702 without any type of understanding of what it is passing to the LP 702. In such an embodiment, it is only the physician's RNID 732 that knows what is being done, and confirmations received by the RNID 732 from the LP 702 (via the SID 712 and the LNID 722) can simply be confirmations of whether the write and/or read commands were successfully performed. Where the SID 712 functions as a smart node, the SID 712 can interpret the commands that originated from the RNID 732, and the SID 712 can issue commands to the LP 702, such as, a command to increase or decrease a stimulation voltage level or some other operational parameter, or the like. Where the SID 712 functions as a smart node, the SID 712 can wait to receive multiple commands, e.g., associated with an entire programming file, before providing the commands to the LP 702. Additionally, where the SID 712 functions as a smart node it may convert commands from one format that is understood by the RNID 732 to another format that is understood by the LP 702. Additionally, or alternatively, the SID may translate commands received from the LNID before sending the commands to the LP. More generally, and for example, where the SID 712 functions as a smart node, the LNID 712 can receive high level commands from the RNID 732 and use those commands to program and/or otherwise control the LP 702. This can be achieved, for example, by the SID translating high level commands into a set of lower level commands that are sent to the LP and used to program and/or otherwise control the LP. By contrast, where the SID 712 functions as a dumb node, the LNID 712 may simply receive and pass on low level commands from the RNID 732 to the LP 702, such as write value A to memory location B, or read value C from memory location D, and/or the like.

In accordance with certain embodiments of the present technology, the SID 712 acts as a data buffer for the LP 702, and more specifically can act as a data buffer between the LP 702 and the LNID 722. For example, when there is no communication link established between the SID 712 and the LNID 722, the SID 722 can from time to time (e.g., periodically, or in response to a triggering event) collect diagnostic data from the LP 702, such that once there is a communication link established between the SID 712 and the LNID 722, the LNID 722 can upload the data (that the SID 712 obtained from the LP 702) from the SID 712, and pass that data onto the RNID 732. Such an embodiment provides for various benefits including reducing memory requirements of the LP 702 and/or allowing for a greater amount of LP diagnostic data collection than would be possible if the LP 702 had to store all such data on its own. Such an embodiment can also reduce the 'session time' when there is a communication link established between the LNID 722 and the RNID 732, because the conducted communication channel between the LP 702 and the SID 712 is bandwidth limited compared to the RF communication channel between the SID 712 and the LNID 722.

Such an embodiment can also reduce and/or spread the impact that a lengthy conducted communication link can have on the battery of the LP 702. Additionally, such an embodiment can allow the SID 712 to collect data from the LP 702 when the orientation of the LP 702 (which may change based on the posture the patient) is better suited for performing conducted communication.

The LNID 722 can be, e.g., a smart phone, a smart watch, a smart home hub, a tablet computer, laptop computer, or a bedside monitor. Such a bedside monitor can be, for example, the Merlin@Home™ transmitter available from Abbott Laboratories (headquartered in Abbott Park, Illinois, USA), but is not limited thereto. Such a smart home hub can be, for example, an ECHO™ available from Amazon Inc. (headquartered in Seattle, Washington, USA), a NEST HUB™ available from Google Inc. (headquartered in Mountain View, California, USA), or a HomePod™ available from Apple Inc. (headquartered in Cupertino, California, USA). In accordance with specific embodiments of the present technology, the LNID 722 is capable of performing RF communication, as well as connecting to and communicating via one or more communication networks 742, which can be the Internet, a local area network (LAN), a wide area network (WAN), a wireless network, an intranet, a private network, a public network, a switched network, combinations of these, and/or the like. Examples of various communication protocols that may be used by the LNID 722 to communicate with the SID, as well as the communication network(s) 742, include: one or more Wi-Fi protocols, Bluetooth protocols, TCP/IP protocols, HTTP protocols, wireless application protocol (WAP), vendor-specific protocols, customized protocols, but are not limited thereto. More specifically, the LNID 722 includes an antenna and an RF transceiver that enables it to communicate with the SID 712 using RF communication signals, such as, but not limited to, Bluetooth signals, BLE signals, WiFi signals, or MedRadio signals. Additionally, an antenna and the RF transceiver of the LNID 722 can enable the LNID 722 to wirelessly connect to one or more communication network(s) 742, e.g., using WiFi signals, Bluetooth signals, or BLE signals, but not limited thereto. Cybersecurity can be provided by the wireless link, e.g., the BLE link or Wi-Fi link, between the SID and LNID.

In certain embodiments described herein, wherein the SID is an ICM, or other type of an IMD, such as an NV-ICD, the SID is able to communicate via conductive communication, as well as communicate via RF communication. In such embodiments, the ICM may perform conductive communication with one or more LPs 102*a* and/or 102*b*, and the ICM 104 can act as a gateway communication device between the LP(s) 102 and an external programmer 109 and/or a remote monitor. Such a remote monitor can be, e.g., an LNID 722.

In certain alternative embodiments, all or some of the capabilities of both the SID 712 and the LNID 722 can be provided by a smart watch that has electrodes on a housing of the smart watch. Such electrodes, which are in contact with a patient's wrist, can enable conductive communication between the LP 702 and the smart watch, in which case the smart watch can provide a communication gateway between the LP 702 and the RNID 732. Such a smart watch should be configured to provide for both conductive communication and RF communication, and thus, the smart watch should have an antenna that enables it to communicate with one or more communication network(s) 742, and thereby with the RNID 732. Some smart watches already included electrodes on their housing, e.g., for the purpose of obtaining an electrocardiogram (ECG) and/or other purposes. The same electrodes can also be used for performing conductive communication, or the smart watch can include electrodes specifically for the purpose of performing conductive communication. Where a smart watch includes an electrode that can be touched by a finger on the hand of the arm that is not wearing the smart watch (to complete a circuit, for the purpose of obtaining an ECG), the ability of the smart watch to perform conductive communication with the SID 712 should be improved. For example, if a user is wearing a smart watch on their left arm (so that an electrode on the backside of the housing of the smart watch is in contact with the user's left wrist), then the user may touch the front facing electrode (or some other accessible second electrode) with a finger on their right arm in order to provide for improved conductive communication with the SID 712. For another example, if a user is wearing a smart watch on their right arm, then the user may touch a front facing electrode (or some other accessible second electrode) with a finger on their left arm in order to provide for improved conductive communication between the smart watch and the SID 712.

Example SID

Figure 8:
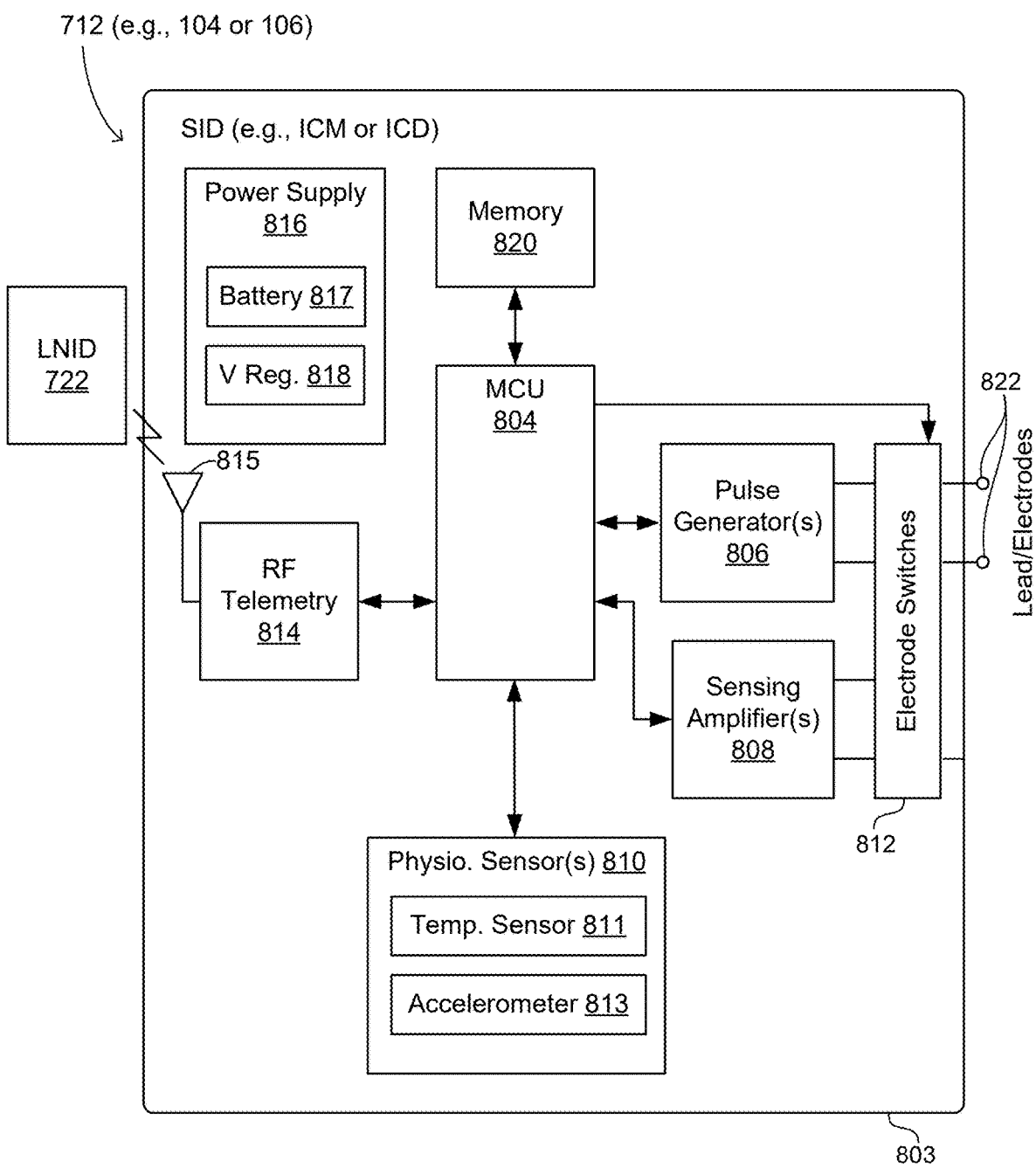
FIG. 8 is a high level block diagram of a second implantable device (SID), introduced in FIG. 7, that is implanted in a patient along with an LP, and is used to enable an RNID to send commands to the LP.

The high level block diagram in FIG. 8 will now be used to describe an example implementation of the second implantable device (SID) 712, which as noted above, can be the ICM 104 or the ICD 106 introduced above in the discussion of FIG. 1, but is not limited thereto. The SID 712 is shown as including a microcontroller unit (MCU) 804, one or more pulse generator(s) 806, one or more sensing amplifier(s) 808, one or more physiologic sensor(s) 810, electrode switches 812, electrodes 822, an RF telemetry module 814, a power supply 816, and memory 820.

As is well known in the art, the MCU 804 (also referred to herein as a control unit or controller) typically includes a microprocessor, or equivalent control circuitry, designed specifically for controlling the delivery of stimulation therapy (if the SID is an IDC) and may further include RAM or ROM memory, logic and timing circuitry, state machine circuitry, and I/O circuitry. Typically, the MCU 804 includes the ability to process or monitor input signals (data) as controlled by a program code stored in a designated block of memory. The details of the design and operation of the MCU 804 are not critical to the technology. Rather, any suitable MCU 804 that includes at least one processor may be used that carries out the functions described herein. The use of microprocessor-based control circuits for performing timing and data analysis functions are well known in the art. Where the SID 712 is an ICD (e.g., 106), the MCU 804 can control the delivery of defibrillation shocks. Where the SID 712 is an ICM, the SID 712 can control the monitoring of various types of physiologic measures. The MCU can also be used to control communication capabilities of the SID. The MCU 804 can be configured to change the format of commands that are received by the SID from the LNID before the SID sends the one or more commands to the LP. Similarly, the MCU 804 can be configured to change the format of acknowledgements that are received by the SID from an LP before the SID sends the acknowledgements to the LNID.

The pulse generator(s) 806 can generate pulses that are provided to the electrodes 822 for performing conductive communication. Where the SID is an ICD or other type of device that performs therapy, the pulse generator(s) 806 can generate pulses for stimulating patient tissue. The electrodes 822 of the SID can be included on one or more leads, or can be located on or adjacent to a housing 803 of the SID 712, e.g., if the SID 712 is an ICM. Where more than two electrodes are available for delivering pulses, the electrode switches 712 can be used to select specific combinations of electrodes under the control of the MCU 804. The pulse generator(s) 806 are controlled by the MCU 804 via appropriate control signals to trigger or inhibit the generation of pulses. Depending upon the implementation, the various components of the MCU 804 may be implemented as separate software modules or the modules may be combined to permit a single module to perform multiple functions. In addition, although described as being components of the MCU 804, some or all of the above discussed modules may be implemented separately from the MCU 804, e.g., using one or more application specific integrated circuits (ASICs) or the like.

The electrode switches 812, which can also be referred to as switching circuitry 812, includes a plurality of switches for connecting the desired electrodes to the appropriate I/O circuits, thereby providing complete electrode programmability. Accordingly, the switching circuitry 812, in response to a control signal from the MCU 804, determines the polarity of the stimulation pulses (e.g., unipolar, bipolar, combipolar, etc.) by selectively closing the appropriate combination of switches (not shown) as is known in the art. The switching circuitry 812 can also switch among the various different combinations of electrodes. The switching circuitry 812 determines the "sensing polarity" of the cardiac signal by selectively closing the appropriate switches, as is also known in the art. In this way, a clinician may program the sensing polarity independent of the stimulation polarity. In certain embodiments, where the SID includes only two electrodes, the switching circuitry 812 can be eliminated.

The sensing amplifier(s) 808 can include, e.g., atrial and/or ventricular sensing amplifiers that are selectively coupled to various combinations of electrodes to provide for various different sensing vectors that can be used, e.g., for detecting the presence of cardiac activity in one or more of the four chambers of the heart. Accordingly, the sensing amplifier(s) 808 can include dedicated sense amplifiers, multiplexed amplifiers or shared amplifiers. The sensing amplifier(s) 808 can also be used to sense conductive communication pulses, or more generally conductive communication signals, that originate from an LP 702 (e.g., 102a or 102b). Each sensing amplifier 808 can employ one or more low power, precision amplifiers with programmable gain and/or automatic gain control, bandpass filtering, and a threshold detection circuit, as known in the art, to selectively sense the signal of interest, which as noted above, can be a cardiac signal and/or a conductive communication signal. The automatic gain control enables the SID 712 to deal effectively with the difficult problem of sensing the low amplitude signal characteristics of atrial or ventricular fibrillation. The outputs of the sensing amplifier(s) 808 are connected to the MCU 804.

Although not specifically shown in FIG. 8, cardiac signals can also be applied to the inputs of an analog-to-digital (A/D) data acquisition system that is configured to acquire intracardiac electrogram signals, convert the raw analog data into a digital signal, and store the digital signals for later processing and/or telemetric transmission to an external programmer or a bedside monitor or personal advisory module (PAM). The data acquisition system can be coupled to various leads and/or electrodes through the switching circuitry 812 to sample cardiac signals across any pair of desired electrodes. The MCU 804 is further coupled to the memory 820 by a suitable data/address bus, or the like, wherein the programmable operating parameters used by the MCU 804 are stored and modified, as required, in order to customize the operation of SID 712 to suit the needs of a particular patient. Such operating parameters can define, for example, a waveshape and vector of each shocking pulse to be delivered to the patient's heart within each respective tier of therapy.

Advantageously, the operating parameters of the SID 712 may be non-invasively programmed into the memory 820 through an RF telemetry circuit 814 in telemetric communication with an external device or bedside monitor, such as the LNID 722. The RF telemetry circuit 814, which can also be referred to as an RF communication subsystem or an RF transceiver 814, is activated by the MCU 804 by a control signal. The RF telemetry circuit 814 enables the SID 712 to wirelessly communicate with the LNID 722 using RF communication signals that are transmitted and received via an antenna 815.

The RF telemetry circuit 814 advantageously allows intracardiac electrograms and status information relating to the operation of the SID 712 (as contained in the MCU 804 or memory 820) to be sent to the LNID 722 through an established communication link. An internal warning device, not specifically shown, may be provided for generating perceptible warning signals to the patient via vibration, voltage or other methods.

The memory 820 may include instructions operable to cause the MCU 804 to perform the methods, or portions thereof, described herein. In one embodiment, the memory 820 may comprise a non-volatile, non-transitory computer readable medium and/or volatile memory containing such instructions. Alternatively, the MCU 804 may include an internal computer readable medium or memory including the instructions.

The physiologic sensors 810 can include a temperature sensor 811, an accelerometer 813, and/or other types of physiologic sensors. The physiological sensor(s) 810 may further be used to detect changes in cardiac output, changes in the physiological condition of the heart, or diurnal changes in activity, or the like. While shown as being included within the SID 712, it is to be understood that one or more of the physiologic sensor(s) 810 may also be external to the SID 712, yet still be implanted within or carried by the patient. Other types of physiologic sensors are also known, for example, sensors that sense the oxygen content of blood, respiration rate and/or minute ventilation, pH of blood, ventricular gradient, stroke volume, cardiac output, contractility, etc.

The power supply 816, which can include a battery 817 and a voltage regulator 818, provides operating power to all of the circuits or subsystem shown in FIG. 8. The specific type of battery 817 included in the SID 712 can vary depending on the capabilities of SID 712. If the SID 712 is an ICD that provides shocking therapy, the battery 817 should be capable of operating at low current drains for long periods, and then be capable of providing high-current pulses (for capacitor charging) when the patient requires a shock pulse. The battery 817 should also have a predictable discharge characteristic so that elective replacement time can be detected. Accordingly, appropriate batteries are employed. One or more voltage regulators 818 can step up
or step down a voltage provide by the battery 817 to produce
one or more predetermined voltages useful for powering the
various circuits or subsystems of the SID 712.

The SID 712 can include additional and/or alternative
types of circuits or subsystems, not specifically shown in
FIG. 8. For example, the SID 712 can also include an
impedance measurement circuit that can be used, e.g., for
measuring respiration or minute ventilation; measuring tho-
racic impedance for determining shock thresholds; detecting
when the device has been implanted; measuring respiration;
and detecting the opening of heart valves, etc. Such an
impedance measurement circuit can be coupled to the
switching circuitry 812 so that any desired combination of
electrodes 822 may be used for measuring impedance.

The RF telemetry circuit 814, which is communicatively
coupled to the MCU 804, can be a Bluetooth Low Energy
(BLE) radio, or some other RF communication subsystem,
and may be implemented as an RF integrated circuit (IC).
The remaining set of circuits or subsystems of the SID 712
shown in FIG. 8, or just a subset thereof, can be imple-
mented in a custom application specific IC (ASIC), which
can also be referred to as a custom chip. In other words, the
terms IC and chip are used interchangeably herein. Depend-
ing on the specific function of the SID 712, the SID may
include additionally IC's. In certain embodiments, a custom
IC can host the SID's application and have all the associated
circuits for sensing, pacing, high voltage (HV) therapy, etc.
The RF chip, which is used to provide RF communication,
can include a high-speed (aka high frequency) crystal oscil-
lator. The connection between the RF chip and a custom chip
is typically a standard serial interface, such as serial periph-
eral interface (SPI) and a few general-purpose input-outputs
(GPIO), but can alternatively or additionally include a
parallel interface.

Example LNID

Figure 9:
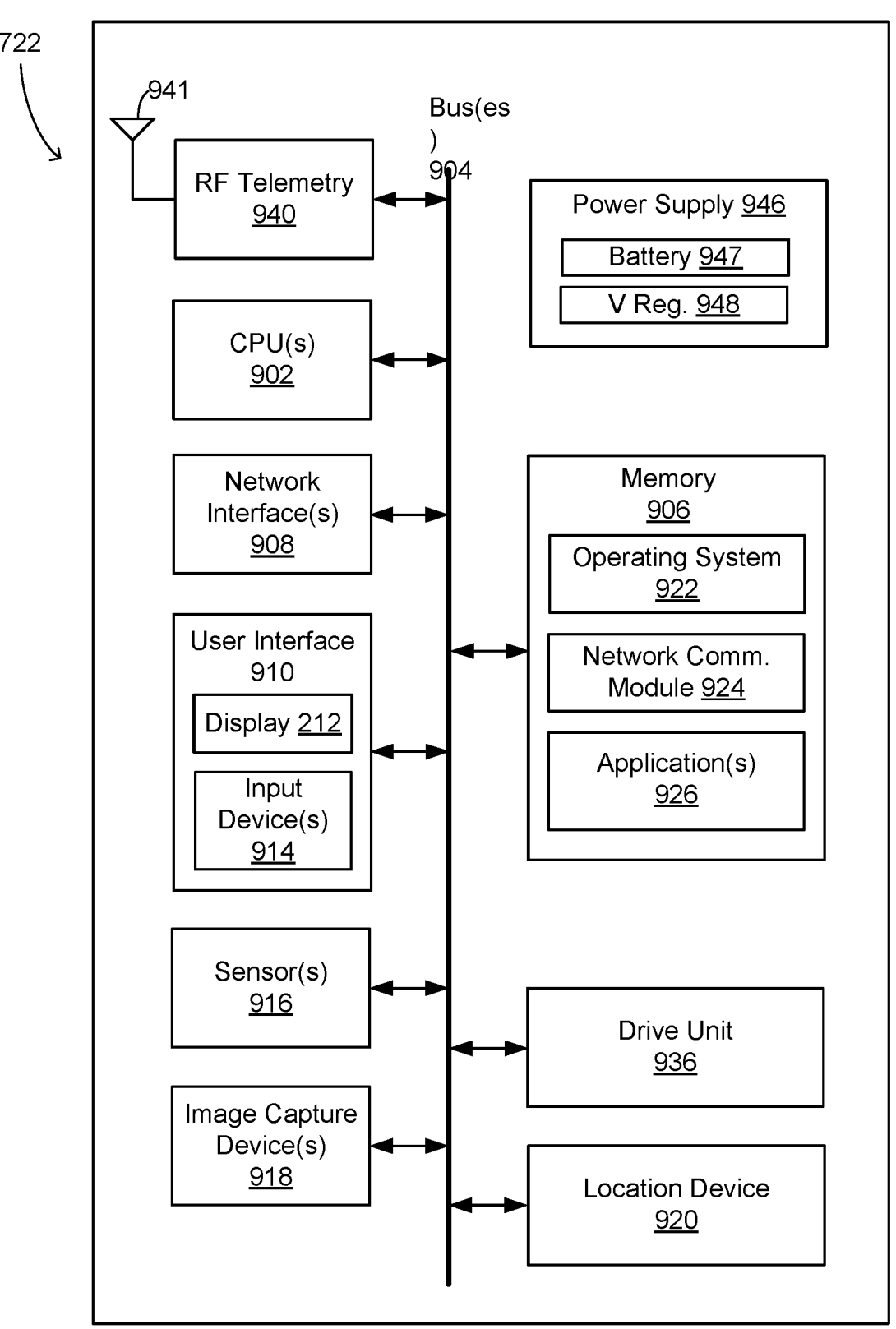
FIG. 9 is a high level block diagram of a local non-implanted device (LNID), introduced in FIG. 7, that is located in close proximity to the patient within which an LP is implanted, and is used to enable an RNID to send commands to the LP.

The high level block diagram in FIG. 9 will now be used
to describe an example implementation of the local non-
implanted device (LNID) 722, which as noted above, can be
a smart phone, a smart watch, a tablet computer, laptop
computer, or a bedside monitor, but is not limited thereto.
Referring to FIG. 9, the LNID 722 is shown as including one
or more processors (e.g., CPU's) 902, one or more network
or other communication interfaces 908, a user interface 910,
a memory 906, a drive unit 936, and one or more commu-
nication buses 904 for interconnecting these and other
components. The communication buses 904 optionally
include circuitry (sometimes called a chipset) that intercon-
nects and controls communication between system compo-
nents. The user interface 910 includes a display device 912
and one or more input devices 914. The LNID 722 is also
shown as including an RF telemetry circuit 940, and a power
supply 946.

In some implementations, the display device 912 is inte-
grated with the device (e.g., housed in the same chassis as
the CPU and memory, such as with a smartphone, a smart
watch or a tablet computer). In some other implementations,
the display device 912 is separate from other components of
the LNID 722 (e.g., a separate device from the device that
houses the CPUs 902 and memory 906, such as with a
desktop computer with a "tower" chassis housing the CPU
and memory and a separate display device). Where the
LNID 722 is a mobile device, such as a smart phone, tablet
computer, smart watch, a laptop computer, or the like, the
display device 912 is most likely integrated with the device. In some embodiments, the CPU(s) 902 can be configured to
change the format of commands that are received by the
LNID from the RNID before the LNID sends the commands
to the SID. Similarly, the CPU(s) 902 can be configured to
change the format of acknowledgements that are received by
the LNID from the SID before the LNID sends the acknowl-
edgements to the RNID.

In some implementations, the input device(s) 914 include
one or more of: a mouse or similar pointing device, a
keyboard, a touch-sensitive surface (e.g., a touch pad, a
touch-sensitive display), a joystick, and/or one or more
buttons. In some implementations, the display device 912 is
a touch screen (i.e., a touch-sensitive display) that, as
described below, may display a virtual keyboard.

In some implementations, the LNID 722 includes addi-
tional input devices, such as an audio input device (e.g., a
microphone). In some implementations, the LNID 722
includes an audio output device (e.g., a speaker, head-
phones).

In some implementations, the LNID 722 also includes one
or more sensors 916 (e.g., accelerometer, magnetometer,
proximity sensor, gyroscope), an image capture device 918
(e.g., a camera device or module and related components),
and a location device 920 (e.g., a Global Positioning System
(GPS) receiver or other navigation or geolocation device and
related components).

The memory 906 can be used to store software and/or
firmware that controls the LNID 722, as well to store
machine readable executable code. Further, the memory 906
can also store commands and/or other data that is/are to be
sent to the SID 712, as well as commands and/or other data
that is/are to be sent to the LP 702, with the SID 712 acting
as a communication gateway between the LNID 722 and the
LP 702. The memory 906 can also store data that is obtained
from the SID 712 and is to be provided to the RNID 732. The
data that the LNID 722 obtains from the SID 712 can be data
sensed by the SID 712, as well as data that is provided by
the LP 702 to the SID 712, in those embodiments where the
SID 712 is acting as a communication gateway between the
LNID 722 and the LP 702.

The memory 906 can comprise various different types of
memory, including non-volatile and volatile memory. For
example, the memory 906 can include high-speed random
access memory, such as DRAM, SRAM, DDR RAM or
other random access solid state memory devices; and may
include non-volatile memory, such as one or more magnetic
disk storage devices, optical disk storage devices, flash
memory devices, or other non-volatile solid state storage
devices. The memory 906 may optionally include one or
more storage devices remotely located from the CPU(s) 902.
The memory 906, or alternatively the non-volatile memory
device(s) within memory 906, comprises a non-transitory
computer readable storage medium. In some implementa-
tions, the memory 906 or the computer readable storage
medium of memory 906 store the following programs,
modules and data structures, or a subset thereof, including:
an operating system 922, network communication module
924, and one or more applications 926.

A drive unit 936, e.g., a hard drive, but not limited thereto,
can also be used to store software that controls the LNID
722, as well as data obtained from the SID 712 and/or LP
702, and commands and/or other data that the LNID 722 is
to pass on from the RNID 732 to the SID 712 and/or the LP
702. The memory 906 and the drive unit 936 can include a
machine readable medium on which is stored one or more
sets of executable instructions (e.g., apps) embodying one or
more of the methodologies and/or functions described herein. In place of the drive unit 936, or in addition to the drive unit, the LNID 722 can include a solid-state storage device, such as those comprising flash memory or any form of non-volatile memory.

The terms "machine-readable medium" and "processor readable storage device" as used herein should be taken to include all forms of storage media, either as a single medium or multiple media, in all forms; e.g., a centralized or distributed database and/or associated caches and servers; one or more storage devices, such as storage drives (including e.g., magnetic and optical drives and storage mechanisms), and one or more instances of memory devices or modules (whether main memory, cache storage either internal or external to a processor, or buffers. The term "machine-readable medium," "computer-readable medium," and "processor readable storage device" shall be taken to include any tangible non-transitory medium which is capable of storing or encoding a sequence of instructions for execution by the machine and that cause the machine to perform any one of the methodologies. The term "non-transitory medium" expressly includes all forms of storage drives (optical, magnetic, etc.) and all forms of memory devices (e.g., DRAM, Flash (of all storage designs), SRAM, MRAM, phase change, etc., as well as all other structures designed to store information of any type for later retrieval.

The RF telemetry circuit 940 enables the LNID 722 to wirelessly communicate with the SID 712 using RF communication signals that are transmitted and received via an antenna 941. The RF telemetry circuit 940, which can also be referred to as an RF communication subsystem or an RF transceiver 940, is activated by a CPU 902 by a control signal.

The memory 906, the drive unit 936 and/or other types of storage media of the LNID 722 can be referred more generally herein as a data store. Further, because such storage media is part of the LNID 722, such storage media can be referred to as a local data store, so as to distinguish it from a remote data store associated with the RNID 732. The operating system 922 includes procedures for handling various basic system services and for performing hardware dependent tasks, as well as obtaining readings from sensors 916.

The network communication module 924 facilitates communication with other devices and computers (e.g., the RNID 732) via the one or more communication network interfaces 908 (wired or wireless) and one or more communication networks 742, such as the Internet, other wide area networks, local area networks, metropolitan area networks, and so on. The network interface(s) 908 of the LNID 722 enable the LNID to communicate with the RNID 732 over one or more communication networks 742. In some implementations, the location module 938 determines the location of the LNID 722 (e.g., using GPS or other similar systems, location identification by IP address, etc.).

The power supply 946, which can include a battery 947 and a voltage regulator 948, provides operating power to all of the circuits or subsystem shown in FIG. 9. One or more voltage regulators 948 can step up or step down a voltage provide by the battery 947 to produce one or more predetermined voltages useful for powering the various circuits or subsystems of the LNID 722.

Although FIG. 9 shows an example of an LNID 722, FIG. 9 is intended more as functional description of the various features which may be present in an LNID 722 than as a structural schematic of the implementations described herein. In practice, and as recognized by those of ordinary skill in the art, items shown separately could be combined and some items could be separated.

Methods for Sending Commands from an RNID to an LP

The high level flow diagram of FIG. 10 will now be used to describe certain embodiments of the present technology that enable a remote non-implantable device (RNID) to program, and more generally send commands to, a leadless pacemaker (LP). Such embodiments are useful in environment, such as the one described above with reference to FIG. 7, where an LP (e.g., 102 or 702) and a second implantable device (SID) (e.g., 712) are both implanted within a patient, and there is a local non-implantable device (LNID) (e.g., 722) that is configured to communicate with the SID when the LNID is in close proximity to the patient within which the SID is implanted (and thus, when the LNID is in close proximity to the SID), and where the RNID is configured to communicate with the LNID. Devices are considered to be in close proximity to one another when they are able to communicate with one another by sending and receiving wireless RF communication signals directly to/from one another. Devices that are not in close proximity to one another can be considered remote from one another.

Referring to FIG. 10, step 1002 involves the RNID (e.g., 732) providing one or more commands to the LNID (e.g., 722) over one or more communication networks (e.g., 742). Step 1004 involves the LNID (e.g., 722) sending the one or more commands, which were received from the RNID (e.g., 732), to the SID (e.g., 712) by transmitting one or more radio frequency (RF) communication signals using an antenna (e.g., 914) of the LNID. The RF communication signals, that are transmitted by the LNID using its antenna, can be Bluetooth signals, BLE signals, WiFi signals, or MedRadio signals, but are not limited thereto. The one or more commands, which are sent by the LNID, and are addressed to the LP, can be or include one or more programming instructions, one or more measurement requests, one or more diagnostics updates, or combinations thereof, but are not limited thereto. Commands, which are sent by the LNID, and are addressed to the LP, can also be used to perform tests on the LP. As explained herein, command(s) provided by the RNID may be translated and/or reformatted by the LNID and/or the SID before the command(s) are sent to and received by the LP.

Step 1006 involves the SID (e.g., 712) receiving the one or more commands from the LNID (e.g., 722) by receiving the one or more RF communication signals (which were transmitted by the LNID at step 1004) using an antenna (e.g., 815) of the SID. Step 1008 involves the SID (e.g., 712) sending the one or more commands to the LP (e.g., 702 or 102) by transmitting one or more conductive communication signals using electrodes (e.g., 822) of the SID. In accordance with certain embodiments, the SID acts as a communication gateway that converts RF communication signals to conductive communication signals and converts one or more data packets including the programming instructions from a first communication protocol that is used by the LNID to a second communication protocol that is used by the LP. In accordance with certain embodiments, conductive communication pulses of conductive communication signals are delivered during cardiac refractory periods that are identified or detected by the SID. In accordance with certain embodiments, conductive communication pulses are sub-threshold, i.e., they are below the capture threshold for the patient.

Step 1010 involves the LP (e.g., 102 or 702) receiving the one or more commands from the SID (e.g., 712) by receiving the one or more conductive communication signals using electrodes (e.g., 102) of the LP. Step 1012 involves the LP (e.g., 102 or 702) performing one or more command responses based on the one or more commands that origi-
nated from the RNID (e.g., 732). The one or more com-
mands that originate from the RNID and are eventually
received by the LP can be or include one or more program-
ming instructions, one or more measurement requests, one
or more diagnostics updates, or combinations thereof, but
are not limited thereto. The LP's command responses to the
commands the LP receives can be, e.g., updating a program-
mable feature of the LP, obtaining a measurement and
providing the measurement to the RNID, and/or providing
stored data to the RNID, but is not limited thereto. The
stored data that the LP sends to the RNID can include, e.g.,
EGM data, battery related data, sensor data, arrhythmic
episode data, patient diagnostic data, LP diagnostic data,
and/or the like.

A format of the command(s), that were sent by to the LP
(e.g., 102 or 702) by the RNID (e.g., 732) can be changed
by the LNID prior to the command(s) being sent from the
LNID (e.g., 722) to the SID (e.g., 712). Additionally, or
alternatively, a format of the command(s) can be changed by
the SID prior to the SID (e.g., 712) sending the command(s)
to the LP (e.g., 102 or 702). The LNID and/or the SID can
also translate commands. More specifically, in accordance
with certain embodiments of the present technology, a
format of the one or more commands changes when the one
or more commands are sent from the LNID to the SID,
and/or when the one or more commands are sent from the
SID to the LP. Alternatively, a format of the command(s)
originating from the RNID remains the same when the
command(s) are sent from the LNID to the SID, and from
the SID to the LP. More generally, the command(s) origi-
nating from the RNID can by translated and/or reformatted
as they pass through the LNIP and/or the SID on the way to
the LP, or vice versa. In other words, the command(s)
received by the LP need not be identical to the command(s)
originally transmitted by the RNID. For example, a set of
commands may get translated at one or more levels into
another set of commands that are equivalent to the original
commands and are appropriate for the target device, e.g., the
LP. For an example, a single complex command originating
from the RNID, such as "interrogate all", can get translated
into a set of many simpler commands appropriate for the LP,
such as "read address 0x1001 thru 0x1010", "read address
0x1011 thru 0x1020", etc. In other words, the LNID can
translate one or more commands from a first set of
command(s) to a second set of command(s), before the
command(s), or the translated version thereof, are sent to the
SID. For another example, the RNID may send a single
"interrogate all" command, and that single command can
then be translated by the LNID (and/or the SID) into a set of
multiple interrogate commands (e.g., one to get clinical
parameters, one to get trims, one to get resettable diagnos-
tics, etc.), before such commands are provided to the LP. It
is noted that the one or more commands that originate from
the RNID and are eventually received by LP are referred to
herein as the one or more commands, even if the one or more
commands are translated and/or reformatted before being
received by the LP.

In accordance with certain embodiments of the present
technology, the one or more RF communication signals sent
from the RNID (e.g., 732) to the LNID (e.g., 722) are
encrypted. Additionally, in accordance with certain embodi-
ments of the present technology, the one or more RF
communication signals sent from the LNID (e.g., 722) to the
SID (e.g., 712) are encrypted. By contrast, the one or more
conductive communication signals sent from the SID to the
LP need not be encrypted, but optionally can be encrypted.

It is beneficial to encrypt the RF communication signals sent
from the RNID (e.g., 732) to the LNID (e.g., 722), because
such signals could be potentially snooped and/or modified
by a nefarious party, such as a hacker or cybercriminal.
Similarly, it is beneficial to encrypt the RF communication
signals sent from the LNID (e.g., 722) to the SID (e.g., 712),
because such signals could be potentially snooped and/or
modified by a nefarious party, such as a hacker or cyber-
criminal. By contrast, it would be virtually impossible, or at
least very difficult, for a nefarious party to snoop and/or
modify the conductive communication signals that are sent
between the SID (e.g., 712) and an LP (e.g., 702 or 102).

In accordance with certain embodiments of the present
technology, prior to step 1002, or as part of step 1002, a
secure communication session is established between the
RNID (e.g., 732) and the LNID (e.g., 722), prior to the
RNID sending the programming instructions and/or one or
more other types of commands to the LNID. This way, the
RNID sending command(s) to the LNID, at step 1002,
occurs during the secure communication session established
between the RNID and the LNID.

For the sake of an example, assume the RNID 732 is
implemented using a physician's tablet computer, and the
LNID 722 is implemented using a patient's smart phone. In
accordance with certain embodiments, a patient application
(aka patient app) is installed in the smart phone type LNID
722, and a physician application (aka physician app) is
installed on the tablet computer type RNID 732. During a
period of when an appointment is scheduled between the
physician and the patient, the physician can use their RNID
732 to initiate a session with the LNID 722, by the physician
using a menu on their RNID 732 to select from one of a
plurality of patients with which the physician is authorized
to communicate and program the patient's LP(s) 702. In
certain embodiments, the physician must first use their
authentication credentials to log into their RNID 732, e.g.,
using a password, biometrics, and/or two factor authentica-
tion, after which the physician can be given access to a
patient menu, and more generally the physician app can be
provided with the ability to initiate a session within a patient
via the patient's LNID 722. In response to a physician
selecting a patient with which the physician wants to initiate
a session, the RNID 732 can send a message to the LNID
722 which indicates that the physician (e.g., Doctor X)
wants to initiate a session with the patient (e.g., Patient Y).
The message can be an app-to-app message that is sent
between the physician app and the patient app. Such a
session can be referred to more specifically as a remote
session, since the patient is remotely located relative to the
physician, and vice versa. The patient app on the LNID 722
can generate an authorization code, which can be a one-
time-password (OTP), or the like, which is only valid for a
specified amount of time, e.g., 1 minute, 2 minutes, 5
minutes, or the like. The authorization code can be, e.g., a 6
digit number type of OTP. In accordance with certain
embodiments, the patient can then provide the authorization
code to the physician without using the patient app, and
more specifically, using some type of out-of-loop commu-
nication, such as by using their LNID 722 to text message
the authorization code to the physician's RNID 732, or
calling (or video chatting with) the physician using their
mobile phone type LNID 722 and verbally telling the
physician the authorization code so that the code can be
manually entered by the physician into the RNID 732. The
use of such out-of-loop communication, e.g., implemented
using cellular or Wi-Fi communication, increases security.
More specifically, with such an embodiment, the only way to hack into the session would be to hack or sniff the app-to-app communication between the physician's RNID 732 and the patient's LNID 722, as well as separately hack or sniff the voice call or text chat between the physician's RNID 732 and the patient's LNID 722. This 6 digit number, or other OTP, can then be used as a seed to generate a key (e.g., 256 bit key), using Transport Layer Security (TLS), Secure Sockets Layer (SSL), and/or some other type of encryption. Other variations are also possible, and within the scope of the embodiments described herein. The above described patient app can be one of the application(s) 926 shown in FIG. 9. The above described physician app can be one of the application(s) 1152 shown in FIG. 11.

In accordance with certain embodiments, an end-to-end communication session is established between the RNID (e.g., 732) and the LP (e.g., 102 or 702), during which the LP sends one or more acknowledgment messages to the RNID in response to the LP successfully receiving one or more commands that originated from the RNID. The LP sending the acknowledgement message(s) to the RNID can involve: the LP sending the one or more acknowledgment messages to the SID by transmitting one or more further conductive communication signals using the electrodes of the LP; the SID receiving the one or more acknowledgment messages from the LP by receiving the one or more further conductive communication signals using the electrodes of the SID; the SID sending the one or more acknowledgment messages to the LNID by transmitting one or more further RF communication signals using the antenna of the SID; the LNID receiving the one or more acknowledgement messages from the SID by receiving the one or more further RF communication signals using an antenna of the LNID; and the LNID providing the one or more acknowledgment messages to the RNID over one or more communication networks.

In alternative embodiments, an end-to-end communication session is not established between the RNID (e.g., 732) and the LP (e.g., 102 or 702). In certain such embodiments, one or more commands that originate from the RNID (e.g., 732) are sent with a destination address (of an LP) and the command(s) is/are routed via secure transit across a series of intermediate servers to an LNID (e.g., 722), a then to an SID (e.g., 712), and then from the SID to the LP. In such embodiments, the acknowledgement message(s) that are sent from the LP, in response to the LP successfully receiving the command(s) that originated from the RNID, can be sent by the LP with a destination address of the RNID, essentially reversing the flow of messages between the RNID and the LP. Alternatively, the SID (e.g., 712), or the LNID (e.g., 722), can add the destination address of the RNID to acknowledgement message(s) that originated from the LP.

In certain embodiments, the one or more commands that are sent from an RNID 732 to an LP 702 are received by the LP 702 within a relatively short time (e.g., a few seconds, or less) of the RNID 732 sending the command(s). In other embodiments, commands that originate from the RNID 732 and are intended for an LP 702 (e.g., by being addressed to the LP), are temporarily stored by the LNID 722 for a period of time and/or temporarily stored by the SID 712 for a period of time, such that at a later point in time the commands are forwarded to the LP 702. More generally, the sending of commands between the RNID 732 and the LP 702 can be performed using asynchronous communication, or alternatively using synchronous communication, or a combination thereof.

Example RNID

Figure 11:
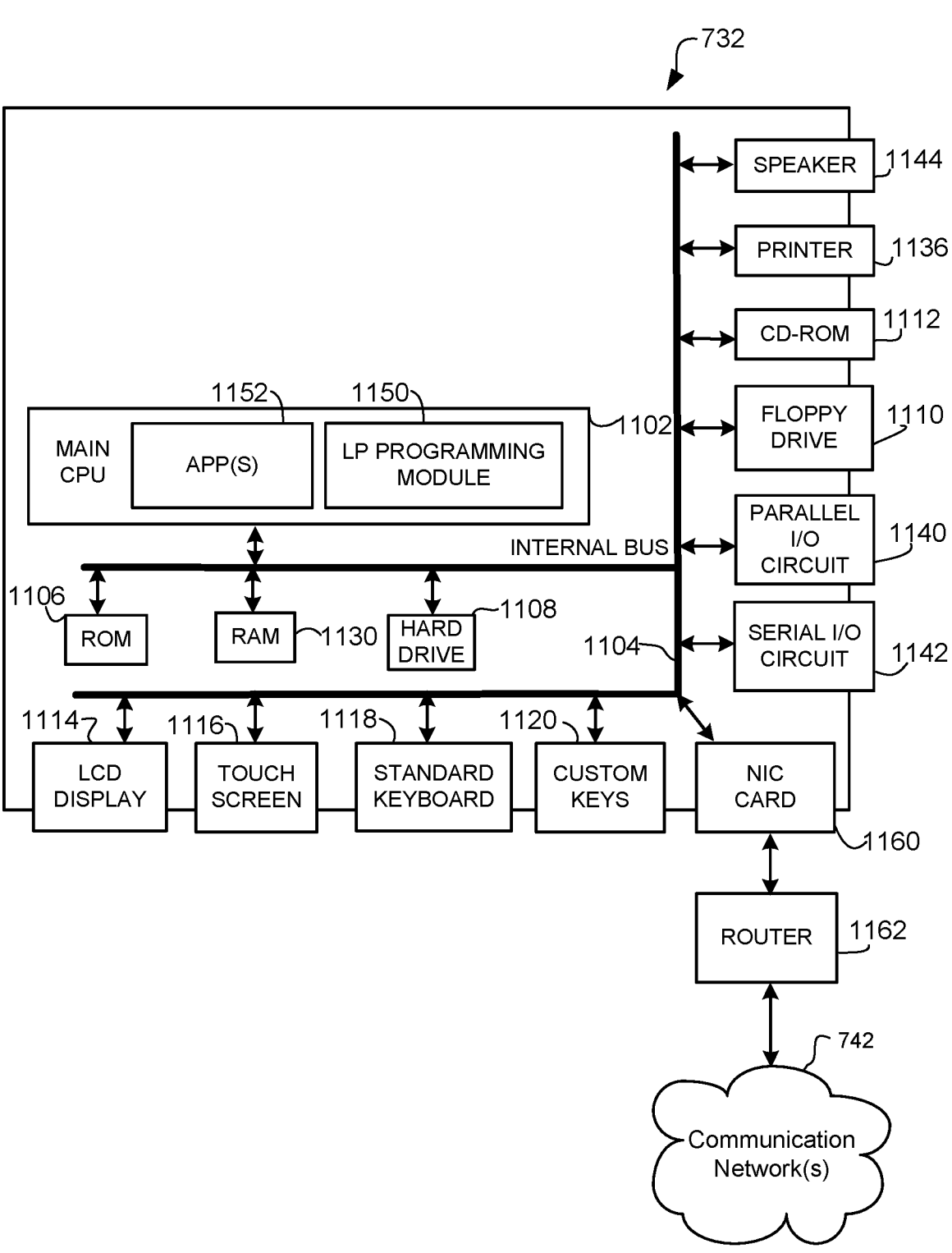
FIG. 11 is a high level block diagram of an RNID, introduced in FIG. 7, that can be used to remotely program, or more generally send commands to, an LP.

FIG. 11 illustrates example components of an of the RNID 732, introduced in FIG. 7, that can be used to remotely program, or more generally send commands to, an LP 702 (e.g., 102). The commands that originate from the RNID 732 and are destined for an LP 702 (e.g., 102) can include programming instructions, measurement requests, diagnostics updates, or combinations thereof, but are not limited thereto. Such commands can include an address or some other unique identifier of the LP, in order to indicate that the intended recipient of the commands is the particular LP. Referring briefly back to FIG. 7, in certain embodiment the RNID 732 can also be used to analyze EGM segments obtained and stored by the LP 702 and/or the SID 712. More generally, the RNID 732 may permit a physician or other authorized user to program the operation of the LP 702 and/or to retrieve and display information received from the LP 702 such as EGM data and device diagnostic data. Depending upon the specific programming of the RNID 732, the RNID 732 may also be capable of processing and analyzing data received from the LP 702 and/or the SID 712, for example, render preliminary diagnosis as to medical conditions of the patient or to the operations of the LP 702. Additionally, the RNID 732 is capable of accepting the various user inputs, in response to which the RNID 732 can generated commands that are to be send to an LP 702.

Now, considering the components of the RNID 732 by reference to FIG. 11, operations of the RNID 732 can be controlled by a CPU 1102, which may be a generally programmable microprocessor or microcontroller or may be a dedicated processing device such as an Application Specific Integrated Circuit (ASIC) or the like. Software instructions to be performed by the CPU can be accessed via an internal bus 1104 from a Read Only Memory (ROM) 1106 and Random Access Memory (RAM) 1130. Additional software may be accessed from a hard drive 1108, floppy drive 1110, and CD ROM drive 1112, or other suitable permanent mass storage device. Depending upon the specific implementation, a Basic Input Output System (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 1114 or another suitable computer display device. To this end, the CPU may, for example, display a menu of specific programming parameters of the LP 702 to be programmed or may display a menu of types of diagnostic data to be retrieved and displayed. In response thereto, the physician enters various commands via either a touch screen 1116 overlaid on LCD display 1114 or through a standard keyboard 1118 supplemented by additional custom keys 1120, such as an emergency WI (EWI) key. The EWI key sets the LP 702 to a safe WI mode with high pacing outputs. This ensures life-sustaining pacing operation in nearly all situations but by no means is it desirable to leave a cardiac stimulation device in the EVVI mode at all times. A graphical user interface (GUI) can be presented on the LCD display 1114, or some other type of display of the RNID 732. Using such an RNID 732, a physician or other authorized personal can display a menu of patients within which one or more LP(s) are implanted, for which the physician or other personal are authorized to program the LP(s) and/or provide other types of commands to the LP(s).

Patient and device diagnostic data stored within the LP 702 can be transferred to the RNID 732. Patient diagnostic information that the RNID 732 receives from an LP 702, in response to the RNID 732 sending commands to the LP 702 requesting such information, can include, for example, measured physiological variables data, recorded EGM data and statistical patient data such as the percentage of paced versus sensed heartbeats. Device diagnostic data can include, for example, information representative of the operation of the LP 702 such as, battery voltages, battery Recommended Replacement Time (RRT) information and the like. Data retrieved from the LP 702 can be stored by the RNID 732 either within a Random Access Memory (RAM) 1130, a hard drive 1108, within a floppy diskette placed within a floppy drive 1110, etc. Additionally, or in the alternative, data may be permanently or semi-permanently stored within a Compact Disk (CD) or other digital media disk, if the overall system is configured with a drive for recording data onto digital media disks, such as a Write Once Read Many (WORM) drive.

The RNID 732 can also include a Network Interface Card ("NIC") 1160 to permit transmission of data to and from other computer systems and a device, such as the LNID 722. Alternatively, the RNID 732 might include a modem for communication via the Public Switched Telephone Network (PSTN). Depending upon the implementation, the modem may be connected directly to internal bus 1104 and may be connected to the internal bus via either a parallel port 1140 or a serial port 1142. The NIC and modem are examples of network interfaces of the RNID that enable the RNID to communicate with the LNID over one or more communication networks. More generally, the RNID 732 includes one or more components that enables the RNID 732 to communicate with the LNID 722 via one or more communication networks 742.

The CPU 1102 can include an LP programming module that can control the performance of the certain steps described above with reference to FIG. 10, or subsets thereof, and/or can instruct the LP 702 to perform certain such steps. The RNID 732 can receive data from the LP 702, including parameters representative of the current programming state of the LP 702. The RNID 732 can also receive EGMs, samples thereof, and/or date indicative thereof from the LP 702. Under the control of the physician, RNID 732 can display the current programming parameters and permits the physician to reprogram the parameters. To this end, the physician enters appropriate commands via any of the aforementioned input devices and, under control of the CPU 1102, the programming commands are converted to specific programming parameters for transmission to the LP 702 to thereby reprogram the LP 702. Prior to reprogramming specific parameters, the physician may control the RNID 732 to display any or all of the data retrieved from the LP 702, including displays of EGMs and statistical patient information. Any or all of the information displayed by RNID 732 may also be printed using a printer 1136.

A speaker 1144 is included for providing audible tones to the user, such as a warning beep in the event improper input is provided by the physician. Telemetry subsystem 1122 may additionally include an input/output circuit 1146 which can control the transmission of analog output signals, such as ECG signals output to an ECG machine or chart recorder. Other peripheral devices may be connected to the RNID 732 via parallel port 1140 or a serial port 1142 as well. Although one of each is shown, a plurality of Input Output (10) ports might be provided.

With the RNID 732 configured as shown, a physician or other authorized user can retrieve, process, and display a wide range of information received from the LP 702 and/or reprogram the LP 702, including configurations of pacing parameters, if needed. The descriptions provided herein with respect to FIG. 11 are intended merely to provide an overview of the operation of the example RNID 732 and are not intended to describe in detail every feature of the hardware and software of the device and are not intended to provide an exhaustive list of the functions performed by the device.

FIG. 11 is used to describe just one example implementation of the RNID 732. Other implementations of the RNID 732 are also possible and within the scope of the embodiments of the present technology. For example, the RNID 732 can be implemented by a server including a web portal, which can also be referred to as a web portal server. Alternatively, or additionally, the RNID 732 (or portions thereof) can be implemented using a cloud computing system. More generally, the RNID 732 can be implemented using one or more processors that implement applications defined by software that is accessed by the processor(s). Other variations are also possible and within the scope of the embodiments of the present technology.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in the various flow diagrams. It would also be possible to just perform a subset of the steps shown in the various flow diagrams. For another example, it is possible to change the boundaries of some of the block diagrams.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are example embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

34

What is claimed is:

1. For use with a leadless pacemaker (LP) configured to be implanted within a patient, a second implantable device (SID) that is also configured to be implanted within the patient, a local non-implantable device (LNID) that is configured to communicate with the SID when the LNID is in close proximity to the patient within which the SID is implanted, and a remote non-implantable device (RNID) that is configured to communicate with the LNID, a method for enabling the RNID to send one or more commands to the LP, the method comprising:

the RNID providing one or more commands to the LNID over one or more communication networks;

the LNID sending the one or more commands to the SID by transmitting one or more radio frequency (RF) communication signals, which include the one or more commands, using an antenna of the LNID;

the SID receiving the one or more commands from the LNID by receiving the one or more RF communication signals, which include the one or more commands, using an antenna of the SID;

the SID sending the one or more commands to the LP by transmitting one or more conductive communication signals, which include the one or more commands, using electrodes of the SID;

the LP receiving the one or more commands from the SID by receiving the one or more conductive communication signals, which included the one or more commands, using electrodes of the LP; and the LP performing one or more command responses based on the one or more commands that originated from the RNID;

wherein the one or more commands provided by the RNID may be translated and/or reformatted by at least one of the LNID or the SID before the one or more commands are received by the LP.

2. The method of claim 1, wherein:
the SID acts as a communication gateway that converts RF communication signals to conductive communication signals and converts one or more data packets including the one or more commands from a first communication protocol that is used by the LNID to a second communication protocol that is used by the LP.

3. The method of claim 1, further comprising at least one of the following:

the LNID changing a format of and/or performing a translation of the one or more commands that are received by the LNID from the RNID before the LNID sends the one or more commands to the SID; or the SID changing the format of and/or performing a translation of the one or more commands that are received by the SID from the LNID before the SID sends the one or more commands to the LP.

4. The method of claim 1, wherein:
the one or more communication signals sent from the RNID to the LNID are encrypted;
the one or more RF communication signals sent from the LNID to the SID are encrypted; and
the one or more conductive communication signals sent from the SID to the LP are not encrypted.

5. The method of claim 1, further comprising:
establishing a secure communication session between the RNID and the LNID, prior to the RNID sending the one or more commands to the LNID;
wherein the RNID sending the one or more commands to the LNID occurs during the secure communication session established between the RNID and the LNID.

6. The method of claim 1, further comprising establishing a communication session between the RNID and the LP during which the LP sends one or more acknowledgment messages to the RNID in response to the LP successfully receiving the one or more commands that originated from the RNID, wherein the LP sending the one or more acknowledgement messages comprises:

the LP sending the one or more acknowledgment messages to the SID by transmitting one or more further conductive communication signals, which include the one or more acknowledgement messages, using the electrodes of the LP;

the SID receiving the one or more acknowledgment messages from the LP by receiving the one or more further conductive communication signals, which include the one or more acknowledgement messages, using the electrodes of the SID;

the SID sending the one or more acknowledgment messages to the LNID by transmitting one or more further RF communication signals, which include the one or more acknowledgement messages, using the antenna of the SID;

the LNID receiving the one or more acknowledgement messages from the SID by receiving the one or more further RF communication signals, which include the acknowledgement messages, using the antenna of the LNID; and the LNID providing the one or more acknowledgment messages to the RNID over one or more communication networks.

7. The method of claim 1, wherein:

the SID comprises one of an insertable cardiac monitor (ICM) or a non-vascular implantable cardiac defibrillator (NV-ICD).

8. The method of claim 1, wherein:

the LNID comprises one of a smart phone, a smart watch, a smart home hub, a tablet computer, a laptop computer or a bedside monitor;

the antenna of the LNID enables the LNID to transmit RF communication signals to, and receive RF communication signals from, the SID; and at least one of an antenna of the LNID or a network interface of the LNID enables the LNID to communicate with the RNID over one or more communication networks.

9. The method of claim 1, further comprising the LP providing diagnostic information to the RNID, wherein the diagnostic information relates to at least one of the LP or the patient within which the LP is implanted, and wherein the LP providing diagnostic information to the RNID comprises:

the LP sending the diagnostic information to the SID by transmitting one or more further conductive communication signals, which include the diagnostic information, using the electrodes of the LP;

the SID receiving the diagnostic information from the LP by receiving the one or more further conductive communication signals, which include the diagnostic information, using the electrodes of the SID;

the SID sending the diagnostic information to the LNID by transmitting one or more further RF communication signals, which include the diagnostic information, using the antenna of the SID;

the LNID receiving the diagnostic information from the SID by receiving the one or more further RF communication signals, which include the diagnostic information, using the antenna of the LNID; and the LNID sending the diagnostic information to the RNID by transmitting one or more messages, which include the diagnostic information, over one or more communication networks.

* * * * *